United States Patent [19]
Hodges et al.

[11] Patent Number: 5,494,672
[45] Date of Patent: Feb. 27, 1996

[54] PSEUDOMONAS PEPTIDE COMPOSITION AND METHOD

[75] Inventors: Robert S. Hodges; William Paranchych, both of Edmonton; Randall T. Irvin, Sherwood Park; Kok K. Lee, Edmonton; Sastry A. Parimi, Edmonton; Dick E. Zoutman, Edmonton; Peter C. Doig, Victoria; Wah Y. Wong, Edmonton, all of Canada

[73] Assignee: S.P.I. Synthetic Peptides Incorporated, Canada

[21] Appl. No.: 638,492

[22] Filed: Jan. 4, 1991

Related U.S. Application Data

[63] Continuation-in-part of Ser. No. 344,565, Apr. 28, 1989.

[51] Int. Cl.$^6$ .......................... A61K 38/00; A61K 38/04; A61K 39/104; A61K 39/02
[52] U.S. Cl. .................... 424/260.1; 424/242.1; 424/184.1; 424/185.1; 530/326; 530/327; 530/328
[58] Field of Search .................... 424/88, 92, 184.1, 424/185.1, 197.11, 242.1, 260.1; 530/300, 330, 323, 329

[56] References Cited

U.S. PATENT DOCUMENTS 4,745,055  5/1988  Schenk et al. .......................... 435/7

FOREIGN PATENT DOCUMENTS 0117367  9/1984  European Pat. Off. ...... C07C 103/52

OTHER PUBLICATIONS

Doig, P. et al., Can. J. Microbiol., (1986) 32:160–166.
Doig, P. et al., Infect. Immun., (1987) 55(6):1517–1522.
Doig, P. et al., Infect. Immun., (1988) 56(6):1641–1646.
Doig, P. et al., Can J. Microbiol., (1989) 35:1141–1145.
Doig, P. et al., Infect. Immun. (1990) 58(1):124–130.
Franklin, A. L. et al., Infect. Immun., (1987) 55(6):1523–1525.
Irvin, R. T. et al., Infect. Immun., (1989) 57(12):3720–3726.
Irvin, R. T. et al., Microbiol. Ecology Health Disease, (1990) 3:39–47.
Irvin, R. T. in "Microbial Cell Surface Hydrophobicicy", Chapter 5 (1990) (R. J. Doyle & M. Rosenberg, Eds.) 137–177.
Lee, K. K. et al., Molecular Microbiology, (1989) 3(11):1493–1499.
Lee, K. K. et al., Infect. Immun., (1989) 57(2):520–526.
Locht, C. & Kieth, J. M., Science, (Jun. 6, 1986) 232(4755):1258–1264.
Paranchych, W., et al., Antibiot. Chemother., 36:49–57.
Sastry, P. A., et al., J. Bacteriology (Nov. 1985) 164(2):571–577.
Sastry, P. A., et al., Can. J. Cell. Biol. (1985) 63:284–291.
Sastry, L., et al., Proc. Natl. Acad. Sci. U.S.A. (1989) 865728–5732.
Saiman, L., et al., Infect. Immun., (1989) 57(9):2764–2770.
Sato, H. & Okinaga, K., Infect. Immun., (1987) 55(8):1774–1778.
Staddon, W., et al., Can. J. Microbiol. (1990) 36:336–339.
Smart, W., et al., Infect. Immun., (1988) 56(1):18–23.
Watts, T. H., et al., Infect. Immun., (1983) 42(1):113–121.

*Primary Examiner*—Hazel F. Sidberry
*Attorney, Agent, or Firm*—Carol A. Stratford; Peter J. Dehlinger

[57] ABSTRACT

A peptide having a sequence corresponding to a C-terminal portion of the *Pseudomonas aeruginosa* pilin protein is disclosed. The peptide is cross-reactive with surface peptides present in certain bacterial and fungal microorganisms, and is effective in inhibiting binding of such organisms to target epithelial cells. The peptide may also be employed in a vaccine composition, for producing immunity against such cross-reactive microorganisms. Also disclosed are methods of preparing peptides which are cross-reactive with the *P. aeruginosa* pilin peptide, and chimeric monoclonal antibodies immunoreactive with the pilin peptide.

1 Claim, 15 Drawing Sheets

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | |
|---|---|---|---|---|---|---|---|---|---|---|---|---|---|---|---|---|---|---|---|---|---|---|---|---|
| | AAG | TGC | ACC | AGT | GAT | CAG | GAT | GAG | CAG | TTT | ATT | CCG | AAA | GGT | TGC | TCT | AGG | | | | | | | |
| | Lys | Cys | Thr | Ser | Asp | Gln | Asp | Glu | Gln | Phe | Ile | Pro | Lys | Gly | Cys | Ser | Arg | | | | | | | (ii) |
| | GCT | TGT | AAA | TCT | ACC | CAG | GAT | CCG | ATG | TTC | ACT | CCG | AAA | GGT | TGT | GAT | AAC | | | | | | | |
| | Ala | Cys | Lys | Ser | Thr | Gln | Asp | Pro | Met | Phe | Thr | Pro | Lys | Gly | Cys | Asp | Asn | | | | | | | (iii) |
| | ACT | TGC | ACC | TCT | ACT | CAG | GAA | ATG | ATG | TTT | ATT | CCT | AAG | GGT | TGT | AAT | AAG | CCT | | | | | | |
| | Thr | Cys | Thr | Ser | Thr | Gln | Glu | Met | Met | Phe | Ile | Pro | Lys | Gly | Cys | Asn | Lys | Pro | | | | | | (iv) |
| | AGC | TGT | GCT | ACT | ACC | GTA | GAT | GCT | AAA | TTC | CGT | CCT | AAT | GGC | TGT | ACT | GAC | | | | | | | |
| | Ser | Cys | Ala | Thr | Thr | Val | Asp | Ala | Lys | Phe | Arg | Pro | Asn | Gly | Cys | Thr | Asp | | | | | | | (v) |
| | GCC | TGT | ACT | TCC | AAC | GCA | GAT | AAC | AAG | TAC | CTG | CCA | AAA | ACC | TGC | CAG | ACT | GCT | ACC | ACT | ACC | ACT | CCG | (vi) |
| | Ala | Cys | Thr | Ser | Asn | Ala | Asp | Asn | Lys | Tyr | Leu | Pro | Lys | Thr | Cys | Gln | Thr | Ala | Thr | Thr | Thr | Thr | Pro | |
| | AAC | ATC | ACC | AAA | ATC | ACC | ACT | ACA | GCT | TGG | AAG | CCC | TGC | TAC | GCT | CCG | AAT | GCT | CCG | AAA | TCC | (vii) |
| | Asn | Ile | Thr | Lys | Ile | Thr | Thr | Thr | Ala | Trp | Lys | Pro | Cys | Tyr | Ala | Pro | Asn | Ala | Pro | Lys | Ser | |
| | ACC | TCG | GGT | ATC | ACT | GGT | TCG | CCT | ACC | AAC | TGG | AAA | ACC | TAC | GCC | CCG | AAC | GCT | CCG | AAA | TCC | (viii) |
| | Thr | Cys | Gly | Ile | Thr | Gly | Ser | Pro | Thr | Asn | Trp | Lys | Thr | Tyr | Ala | Pro | Asn | Ala | Pro | Lys | Ser | |
| | ACC | TGC | ACT | ACT | GGT | TCG | CCG | ACC | AAC | TGG | ACC | GCC | AAC | TAC | GCT | CCG | AAT | TGC | CCG | AAA | TCC | (ix) |
| | Thr | Cys | Thr | Ile | Gly | Ser | Pro | Thr | Asn | Trp | Thr | Ala | Asn | Tyr | Ala | Pro | Asn | Cys | Pro | Lys | Ser | |
| | GGT | TGC | ATC | AGT | AGC | ACT | CCT | GCT | TGG | AAA | CCA | AAC | TAT | GCC | TCT | CCG | AAC | TGC | CCG | AAA | TCC | (x) |
| | Gly | Cys | Ser | Ile | Ser | Thr | Pro | Ala | Trp | Lys | Pro | Asn | Tyr | Ala | Ser | Pro | Asn | Cys | Pro | Lys | Ser | |

Fig. 1

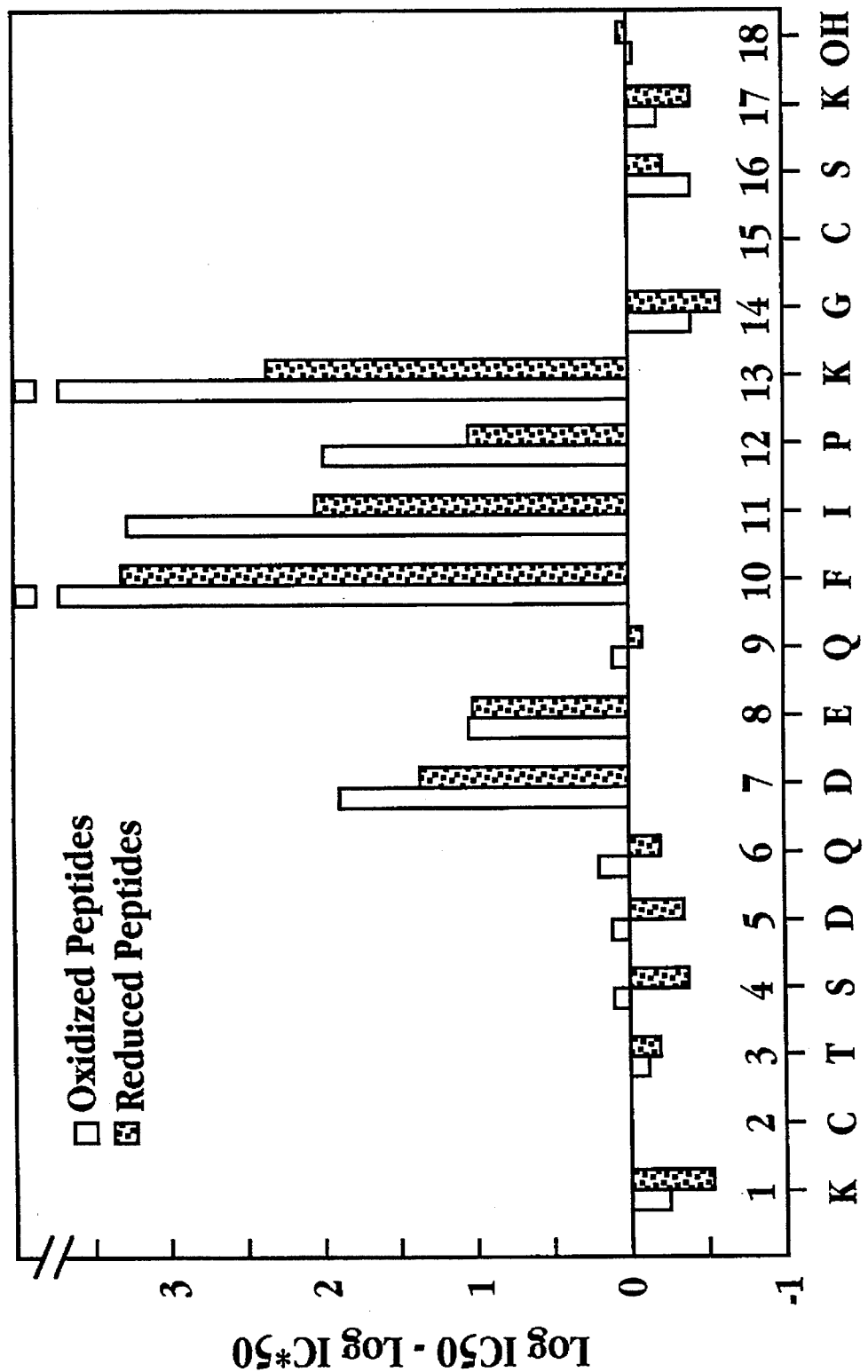

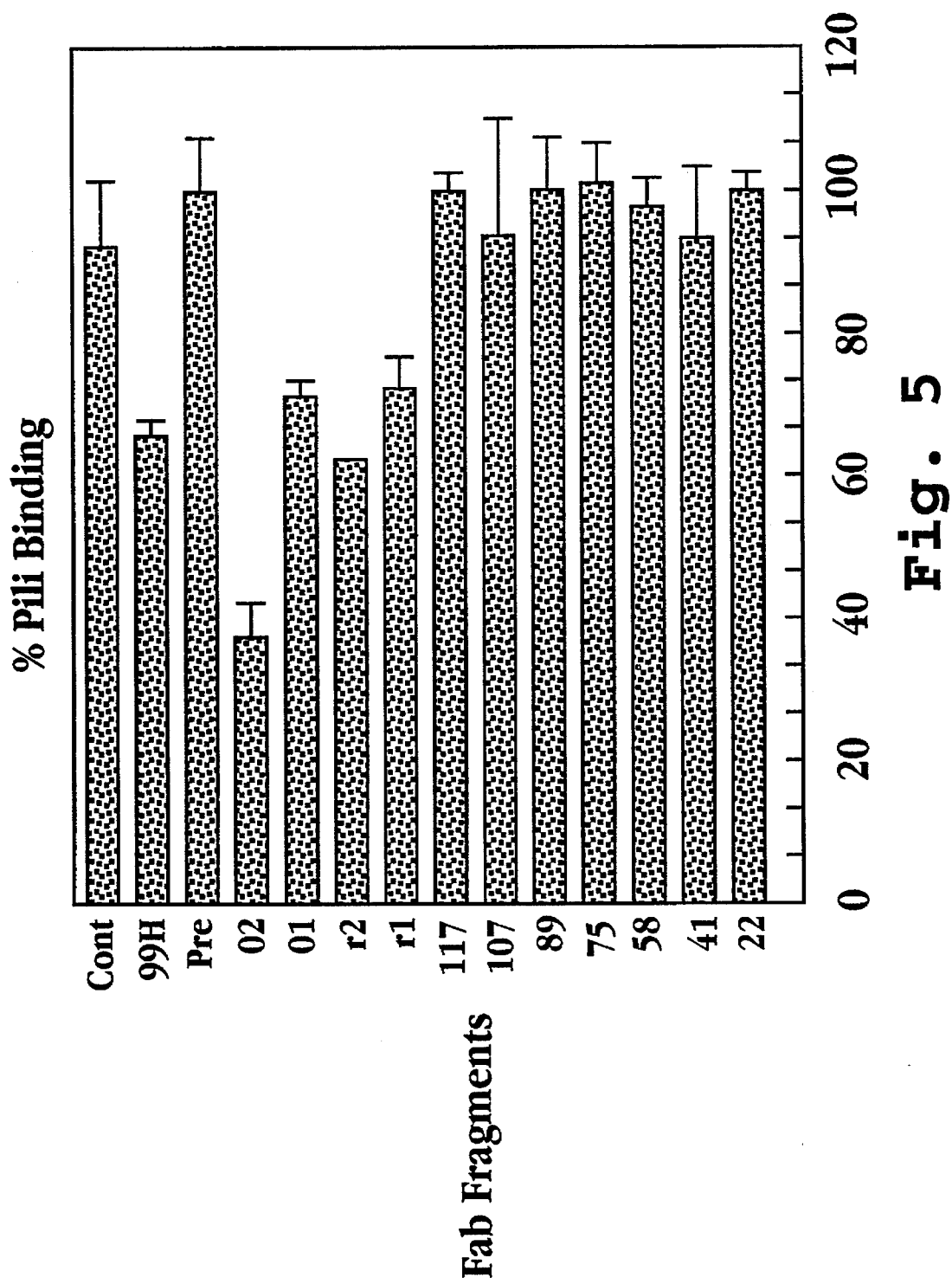

Sequence DNA to determine amino acid sequence of immunoreactive peptide

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: peptide 1

( x i ) SEQUENCE DESCRIPTION: SEQ ID NO:1:

Lys Cys Thr Ser Asp Gln Asp Glu Gln Phe Ile Pro Lys Gly Cys Ser
1               5                   10                  15
Lys ( 2 ) INFORMATION FOR SEQ ID NO:2:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: peptide 2

( x i ) SEQUENCE DESCRIPTION: SEQ ID NO:2:

Lys Cys Thr Ser Asp Gln Asp Glu Gln Phe Ile Pro Lys Gly Cys Ser
1               5                   10                  15
Arg ( 2 ) INFORMATION FOR SEQ ID NO:3:

( i ) SEQUENCE CHARACTERISTICS:
   ( A ) LENGTH: 17 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
   ( C ) INDIVIDUAL ISOLATE: peptide 3

( x i ) SEQUENCE DESCRIPTION: SEQ ID NO:3:

```
Ala  Cys  Lys  Ser  Thr  Gln  Asp  Pro  Met  Phe  Thr  Pro  Lys  Gly  Cys  Asp
1                  5                        10                      15
Asn
```

( 2 ) INFORMATION FOR SEQ ID NO:4:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( C ) INDIVIDUAL ISOLATE: peptide 4

( x i ) SEQUENCE DESCRIPTION: SEQ ID NO:4:

```
Thr  Cys  Thr  Ser  Thr  Gln  Glu  Glu  Met  Phe  Ile  Pro  Lys  Gly  Cys  Asn
1                  5                        10                      15
Lys  Pro
```

( 2 ) INFORMATION FOR SEQ ID NO:5:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( C ) INDIVIDUAL ISOLATE: peptide 5

( x i ) SEQUENCE DESCRIPTION: SEQ ID NO:5:

```
Ser  Cys  Ala  Thr  Thr  Val  Asp  Ala  Lys  Phe  Arg  Pro  Asn  Gly  Cys  Thr
1                  5                        10                      15
Asp
```

( 2 ) INFORMATION FOR SEQ ID NO:6:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: peptide 6

( x i ) SEQUENCE DESCRIPTION: SEQ ID NO:6:

```
Ala Cys Thr Ser Asn Ala Asp Asn Lys Tyr Leu Pro Lys Thr Cys Gln
 1               5                  10                  15

Thr Ala Thr Thr Thr Thr Pro
                20
```

( 2 ) INFORMATION FOR SEQ ID NO:7:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: peptide 7

( x i ) SEQUENCE DESCRIPTION: SEQ ID NO:7:

```
Asn Cys Lys Ile Thr Lys Thr Pro Thr Ala Trp Lys Pro Asn Tyr Ala
 1               5                  10                  15

Pro Ala Asn Cys Pro Lys Ser
                20
```

( 2 ) INFORMATION FOR SEQ ID NO:8:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: peptide 8

( x i ) SEQUENCE DESCRIPTION: SEQ ID NO:8:

```
Thr Cys Gly Ile Thr Gly Ser Pro Thr Asn Trp Lys Ala Asn Tyr Ala
 1               5                  10                  15

Pro Ala Asn Cys Pro Lys Ser
                20
```

( 2 ) INFORMATION FOR SEQ ID NO:9:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide (i i i) HYPOTHETICAL: NO (i v) ANTI-SENSE: NO (v i) ORIGINAL SOURCE:
(C) INDIVIDUAL ISOLATE: peptide 9

(x i) SEQUENCE DESCRIPTION: SEQ ID NO:9:

Thr Cys Gly Ile Thr Gly Ser Pro Thr Asn Trp Lys Thr Asn Tyr Ala
1               5                   10                  15

Pro Ala Asn Cys Pro Lys Ser
            20

(2) INFORMATION FOR SEQ ID NO:10:

(i) SEQUENCE CHARACTERISTICS:
(A) LENGTH: 23 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (v i) ORIGINAL SOURCE:
(C) INDIVIDUAL ISOLATE: peptide 10

(x i) SEQUENCE DESCRIPTION: SEQ ID NO:10:

Gly Cys Ser Ile Ser Ser Thr Pro Ala Asn Trp Lys Pro Asn Tyr Ala
1               5                   10                  15

Pro Ser Asn Cys Pro Lys Ser
            20

(2) INFORMATION FOR SEQ ID NO:11:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (v i) ORIGINAL SOURCE:
(C) INDIVIDUAL ISOLATE: peptide 11

(x i) SEQUENCE DESCRIPTION: SEQ ID NO:11:

Asp Glu Gln Phe Ile Pro Lys
1               5

(2) INFORMATION FOR SEQ ID NO:12:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (v i) ORIGINAL SOURCE:
(C) INDIVIDUAL ISOLATE: peptide 12

(x i) SEQUENCE DESCRIPTION: SEQ ID NO:12:

Asp Pro Met Phe Thr Pro Lys
1               5

(2) INFORMATION FOR SEQ ID NO:13:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (v i) ORIGINAL SOURCE:
(C) INDIVIDUAL ISOLATE: peptide 13

(x i) SEQUENCE DESCRIPTION: SEQ ID NO:13:

Glu Glu Met Phe Ile Pro Lys
1               5

(2) INFORMATION FOR SEQ ID NO:14:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (v i) ORIGINAL SOURCE:
(C) INDIVIDUAL ISOLATE: peptide 14

(x i) SEQUENCE DESCRIPTION: SEQ ID NO:14:

Asp Ala Lys Phe Arg Pro Asn
1               5

(2) INFORMATION FOR SEQ ID NO:15:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (v i) ORIGINAL SOURCE:
(C) INDIVIDUAL ISOLATE: peptide 15

(x i) SEQUENCE DESCRIPTION: SEQ ID NO:15:

Asp Asn Lys Tyr Leu Pro Lys
1               5

PSEUDOMONAS PEPTIDE COMPOSITION AND METHOD

This application is a continuation-in-part of copending U.S. for "Synthetic *Pseudomonas aeruginosa* Pilin Peptide," Ser. No. 344,565, filed Apr. 28, 1989.

FIELD OF THE INVENTION

The present invention relates to Pseudomonas-derived polypeptide antigens, to methods of producing such antigens, and to antibodies immunoreactive against the antigens.

REFERENCES

Adams, M. H. Methods of study of bacterial viruses, p. 443–452. In M. H. Adams (ed.), Bacteriophages. Interscience Publishers, Inc., New York (1959).

Ausubel, F. M., et al., Current Protocols in Molecular Biology, John Wiley and Sons Inc., Media, Pa. (1990).

Beachy, E. H. 1981 J. Infect. Dis. 143: 325–345 (1981).

Boulianne, G. L. et al., Nature 312:643–646 (1984).

Carr, B., et al., Gerontology 35:127–129 (1989).

Cwirla, S. E. et al., Proc. Natl. Acad. Sci. USA 87:6378–6382 (1990).

Devlin, J. J., et al., Science 249: 404 (1990).

Doig, P., et al., Infect. Immun. 56:1641–1646 (1988).

Doig, P., et al., Infect. Immun. 58:124–130 (1990).

Franklin, A. L., et al., Infect. Immun. 55:1523–1525 (1987).

Geyson, H. M. et al., in Synthetic Peptides as Antigens; Ciba Foundation Symposium 119:131–149 (1986).

Irvin, R. T. and Ceri, H., Can. J. Microbiol. 31:268–275 (1985).

Irvin, R. T., et al., Microbial Ecology Health Disease, 3:39–47 (1990).

Lee, K. K., et al., Infect. Immun. 57:520–526 (1989).

Lee, K. K., et al, Inf Immunol, 58:2727–32 (1990).

Marrs, C. F., et al., Am. J. Med. 88 (Suppl 5A): 36S–40S (1990).

McBride, L. J., et al., Clin Chem, 35:2196–2201 (1989).

McEachran, D. W., et al, Can. J. Microbiol. 31:563–569 (1985).

McEachran, D. W., et al., J. Microbiol. Meth. 5:99–111 (1986).

Morrison, S. L., et al., Proc. Natl. Acad. Sci. USA 81:6851–6855 (1984).

Nieto, A., et al., Mol. Immunol. 21:537–543 (1984).

Pasloske, B. L., et al., J Bacteriol, 170:3738–3741 (1988).

Paranchych, W., et al., Can. J. Microbiol. 25:1175–1181.

Paranchych, W. et al., Advan. Microbiol. Phys. 29:53–114 (1988).

Parmley, S. F. and Smith, G. P. Gene 73:305–318 (1988).

Rabbitts, T. H. et al., Nucleic Acids Res. 9:4509–4524 (1981).

Sanger, S., et al., PNAS (USA), 74:5463–5467 (1977).

Sato, H. and Okinaga, K., Infect. Immun. 55: 1774–1778 (1987).

Scott, J. K. and Smith, G. P., Science 249:386–390 (1990).

Sastry, L., et al., Proc. Natl. Acad. Sci. USA 86:5728–5732 (1989).

Sastry, P. A., et al., Can. J. Cell Biol. 63:284–291 (1985).

Staddon, W., et al., Can. J. Microbiol. 36:336–340 (1990).

Todd, T., et al., Am. Rev. Respir. Dis. 140:1585–1589 (1989).

Tsai, C., et al., Anal. Biochem. 119:115–119 (1982).

Worobec, E. A., et al., J. Biol. Chem. 260:938–943 (1985).

zu Putlitz, J., et al., Bio/Technology 8:651–654 (1990).

BACKGROUND OF THE INVENTION

During the past two decades, *Pseudomonas aeruginosa* has been recognized as a pathogen which causes between 10% and 20% of infections in most hospitals. Pseudomonas infection is especially prevalent among patients with burn wounds, cystic fibrosis, acute leukemia, organ transplants, and intravenous-drug addiction. *P. aeruginosa* is a common nosocomial contaminant, and epidemics have been traced to many items in the hospital environment. Patients who are hospitalized for extended periods are frequently affected by this organism and are at increased risk of developing infection. The most serious infections include malignant-external otitis, endophthalmitis, endoconditis, meningitis, pneumonia, and septicemia. The likelihood of recovery from Pseudomonas infection is related to the severity of the patient's underlying disease process. The reported mortality for *P. aeruginosa* pneumonia is as high as 50–80%. Even with the development of newer antibiotics, resistance remains a problem necessitating combined antibiotic treatment for severe *P. aeruginosa* infections.

Various therapies for the management of severe *P. aeruginosa* infections have been evaluated for many years, with particular attention focused on virulence factors. As with most bacterial pathogens, virulence of *P. aeruginosa* is multifactorial and is the product of many interacting variables, involving both the bacterium and the host. Evidence suggests that the initial event in infection is the adherence of microorganisms to epithelial cells of mucosal surfaces (Bleachy). Organisms that are unable to adhere to mucosal surfaces fail to colonize because they are removed by the secretions that bathe the mucosal surfaces (Bleachy). The adherence process is dependent upon the specific recognition between bacteria and epithelial cells.

For a number of gram-negative bacteria, including *P. aeruginosa*, attention has been directed to surface appendages as mediations of adherence. The surface of many gram-negative bacteria, e.g., *Escherichia coli, P. aeruginosa, Moraxella bovis, Neisseria gonorrhea*, are covered with filamentous structures called pili or fimbriae. Pili are composed primarily of protein (pilin) and have been found to act as antigenic determinants when injected into test animals. In *P. aeruginosa*, strain-specific pili, such as those designated PAO, PAK, and CD4, mediate the colonization of the bacteria in humans (Doig,88).

Some *P. aeruginosa* bacteria lacking these pili, either through mutation or loss of the plasmid carrying the pilus gene, are incapable of colonizing mucosa. Apparently, the pili on the surface of the bacterium adhere to the lining of the throat and trachea through specific interactions with epithelial cell receptors. *P. aeruginosa* can utilize both pili and alginate (the principle component of the *P. aeruginosa* capsule) as adhesins to mediate attachment to human respiratory epithelial cells (Doig).

Equilibrium analysis of *P. aeruginosa* binding to human respiratory epithelial cells indicates that the Pseudomonas pilus adhesin has a considerably higher apparent affinity or binding constant than does the alginate adhesin (McEachran, 1985, 1986). These observations suggest that the pilus adhesin is likely the dominant Pseudomonas adhesin in the initiation of an infection (Irvin). Adhesion-mediated anchorage is a prerequisite for the induction of disease by *P. aeruginosa.*

The earlier filed co-pending patent application discloses a *P. aeruginosa* peptide derived from the C-terminal region of the *P. aeruginosa* pilin protein, and specifically, the C-terminal region which includes two Cys residues and the intervening amino acid residues. The derived region of representative peptides vary in length between 14 and 19 amino acid residues, including the two Cys residues, and are prepared in both oxidized (disulfide-linked) and reduced (non-cyclized) form. The peptides (in both reduced and oxidized form) were shown to have the following properties:

(a) ability to bind to human tracheal epithelial cells (TECs) and human buccal epithelial cells (BECs);

(b) ability to inhibit binding of Pseudomonas pilin peptide to tracheal epithelial cells (TECs) and buccal epithelial cells (BECs);

(c) ability to elicit serum antibodies which are immunoreactive with Pseudomonas pilin peptide; and (d) ability to elicit serum antibodies which block binding to Pseudomonas pilin peptide to BECs.

It has now been discovered that the Pseudomonas-derived peptide is able to inhibit binding of unrelated bacterial and fungal organisms to human TECs and/or BECs. Thus, the epithelial cell receptor site(s) which bind the Pseudomonas-derived peptide, and thereby inhibit binding of Pseudomonas pilin (and Pseudomonas bacteria) to TECs and BECs is also involved in binding of other bacterial and fungal organisms to these target cells. It has further been shown, in studies conducted in support of the present invention, that monoclonal antibodies prepared against the Pseudomonas-derived peptide are effective in blocking fungal cell adherence to BECs.

These combined findings show that the Pseudomonas-derived peptide, and antibodies produced in response to the peptides, are capable of inhibiting bacterial and fungal infections in which the infecting microorganism has surface proteins which are antigenically crossreactive with antibodies produced against the C-terminal, disulfide-linked peptide region of *P. aeruginosa* pilin protein.

SUMMARY OF THE INVENTION

The invention includes, in one aspect, a peptide having a sequence corresponding to a C-terminal region of a *P. aeruginosa* pilin protein, and more specifically, to one of the sequences represented as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. Including amino acid variations which are internally consistent among sequences SEQ ID NO:1, SEQ ID NO:2, SEQ ID NO:3, SEQ ID NO:4, SEQ ID NO:5 and SEQ ID NO:6 and among sequences SEQ ID NO:7, SEQ ID NO:8, SEQ ID NO:9 and SEQ ID NO:10.

The peptide of the invention is further characterized by (a) a disulfide linkage between the two Cys (C) residues; (b) immunospecific binding to PK99H or PK34C monoclonal antibody; (c) specific binding to tracheal or buccal epithelial cells; and (d) absence of specific binding to *P. aeruginosa* pilin protein.

In a related aspect, the invention includes a composition for use as a vaccine against infection by bacterial and fungal organisms which have surface proteins which are antigenically crossreactive with antibodies produced against the C-terminal, disulfide-linked peptide region of *P. aeruginosa* pilin protein. The composition includes the above peptide and an immunogenic carrier to which the peptide is attached. In one embodiment, for use as a vaccine against Pseudomonas infection, the peptide is immunoreactive with PK34C monoclonal antibody. In another embodiment, for use as a vaccine against Candida infection, the peptide is immunoreactive with PK99H antibody.

In another aspect, the peptide has an amino acid sequence selected from the group consisting of SEQ ID NO:11, SEQ ID NO:12, SEQ ID NO:13, SEQ ID NO:14, and SEQ ID NO:15. Including amino acid variations which are internally consistent among sequences SEQ ID NO:11, SEQ ID NO:12, SEQ ID NO:13, SEQ ID NO:14 and SEQ ID NO:15 and characterized by: (a) immunospecific binding to a PK99H or a PK34C monoclonal antibody; (b) specific binding to human buccal or human tracheal epithelial cells; and (c) absence of specific binding to *P. aeruginosa* pilin protein.

The peptide composition is employed in a vaccination method of protecting an individual against infection by bacterial and fungal organisms which have surface proteins which are antigenically crossreactive with antibodies produced against the C-terminal, disulfide-linked peptide region of *P. aeruginosa* pilin protein.

Also forming part of the invention is a method of producing a composition for use as a vaccine against infection by bacterial and fungal organisms which have surface proteins which are antigenically crossreactive with antibodies produced against the C-terminal, disulfide-linked peptide region of *P. aeruginosa* pilin protein. The method relies on the selection of random-sequence peptides produced by a vector library of random-sequence polynucleotides, typically corresponding to a random sequence of 5–10 codons. Selection is by peptide binding to a monoclonal antibody immunoreactive with the C-terminal, disulfide-linked peptide region of *P. aeruginosa* pilin protein, and preferably to the PK34C or PK99H monoclonal antibody. The sequence of the selected binding polypeptide can be determined from the polynucleotide coding sequence of the corresponding library vector. From this sequence, the desired polypeptide can be made by synthetic or recombinant means.

Also disclosed is a chimeric monoclonal antibody composed of the variable regions of mouse PK34C or PK99H monoclonal antibody, and the constant regions of a human immunoglobulin G antibody. The antibody can be used to treat infection by bacterial and fungal organisms having surface proteins which are antigenically crossreactive with antibodies produced against the C-terminal, disulfide-linked peptide region of *P. aeruginosa* pilin protein.

In still another aspect, the invention includes a method of treating an infection of the lung caused by a bacterial or fungal organism which have surface proteins which are antigenically crossreactive with antibodies produced against the C-terminal, disulfide-linked peptide region of *P. aeruginosa* pilin protein. The method includes forming an aerosol of the peptide and administering the peptide by inhalation.

These and other objects and features of the present invention will be come more fully apparent when the following detailed description of the invention is read in conjunction with the accompanying drawings.

BRIEF DESCRIPTION OF THE DRAWINGS

FIG. 1 shows the amino acid sequences of Pseudomonas peptides of the invention;

FIG. 2 shows the relative binding affinity of native PAK peptide and PAK peptides with modified C-terminus and N-terminus and peptides containing Ala substitutions at each of the 17 peptide residues except for the Cys residues for monoclonal antibody PK99H;

FIG. 5 is a bar graph showing the percent of PAK pili binding to BECs, after preincubation of BECs with Fab fragments of the antibodies indicated;

FIG. 7 shows fractionated M. catarrhalis proteins stained by immunoblot with polyclonal anti-PAK pili antibody (lane 1), and with protein stain (lane 2) and standards (lane 3);

FIG. 10 shows a Western blot of several Bacteroides strains immunoblotted with PK99H monoclonal antibody;

DETAILED DESCRIPTION OF THE INVENTION

I. Definitions

Figure 3:
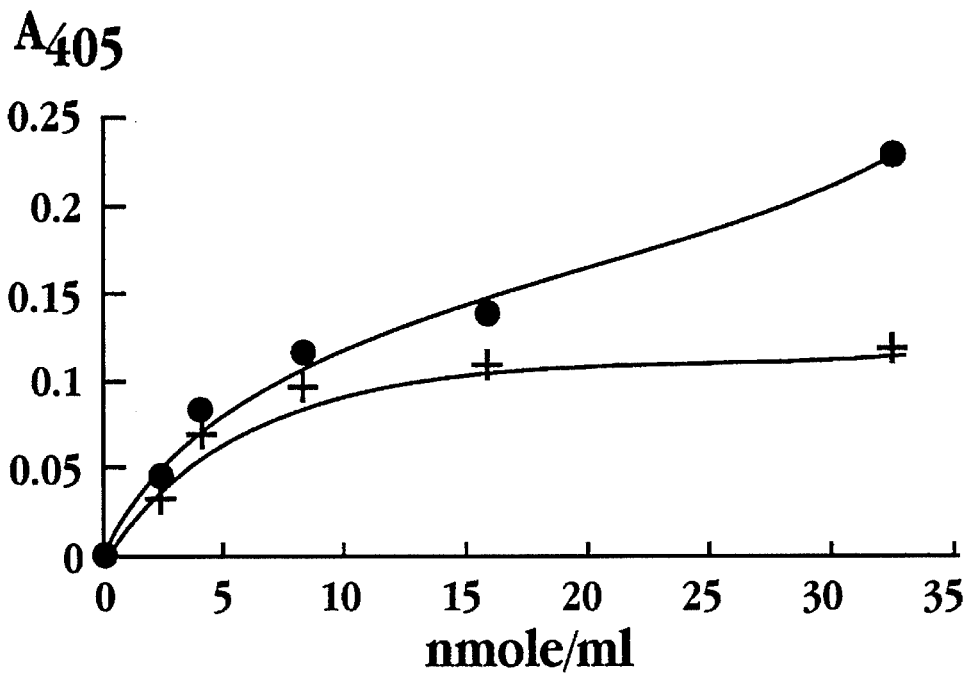
FIG. 3 is a plot showing the binding of synthetic peptide $PAK_{red}$ (solid squares) and $PAK_{ox}$ to human BECs.

The terms "epitope" and "epitopic," as used herein, designate the structural component of a molecule that is responsible for specific interaction with corresponding antibody (immunoglobulin) molecules elicited by the same or related antigen.

The term "antigen," as used herein, means an entity that is recognized by an antibody.

The term "immunogen," as used herein, describes an entity that induces antibody production in the host animal. In some instances the antigen and the immunogen are the same entity, while in other instances the two entities are different.

The term "immunologically mimics" is used herein to mean that an immunogenic polypeptide of this invention is not a natural protein or a cleaved fragment of a natural protein, but a manufactured polypeptide, as by solid phase synthesis or genetic engineering techniques, which polypeptide induces production of antibodies that bind to the inducing polypeptide and also to a corresponding pilin or pilin polypeptide portion.

All amino acid residues identified herein are in the natural or L-configuration unless otherwise specified. In keeping with standard peptide nomenclature, abbreviations for amino acid residues that have been used herein are as follows:

| Symbol | | |
|---|---|---|
| 1 Letter | 3 Letter | Amino Acid |
| Y | TYR | -L-tyrosine |
| G | GLY | -glycine |
| F | PHE | -L-phenylalanine |
| M | MET | -L-methionine |
| A | ALA | -L-alanine |
| S | SER | -L-serine |
| I | ILE | -L-isoleucine |
| L | LEU | -L-leucine |
| T | THR | -L-threonine |
| V | VAL | -L-valine |
| P | PRO | -L-proline |
| K | LYS | -L-lysine |
| N | ASN | -L-asparagine |
| H | HIS | -L-histidine |
| Q | GLN | -L-glutamine |
| E | GLU | -L-glutamic acid |
| W | TRP | -L-tryptophan |
| R | ARG | -L-arginine |
| D | ASP | -L-aspartic acid |
| C | CYS | -L-cysteine |

II. P. aeruginosa Pilin Peptide

FIG. 1 shows the C-terminal amino acid sequences, and corresponding polynucleotide coding sequences, of the pilin protein from ten P. aeruginosa strains which have been sequenced to date. The P. aeruginosa strains or isolates from which the sequences were obtained are given at the left in the figure, and are used herein to designate the particular pilin peptide sequence. Strains PAK, PAO, and 492c have been reported (Doig, 1990), as have strains CD4, KB7, K122, GA1, and TBOU1 (Pasloske). The strain designated PAK(R) is muant PAK strain containing a C-terminal Lys-to-Arg substitution (Sastry). The C-terminal sequences of strains PAK(R), PAO, CD4, K122, KB7, P1, 492C, and TBOU1 were reported in the earlier filed co-pending application.

The corresponding polynucleotide coding sequences for the various strains were determined from published reports, or by sequencing isolated P. aeruginosa genomic material obtained from the individual strains. The genomic material was amplified by polymerase chain reaction (PCR) methods, using degenerate probes corresponding to N-terminal and C-terminal regions of the amino acids sequences shown in the figure, according to conventional procedures (McBride). Sequencing of the amplified genomic material was by dideoxy sequencing, according to standard procedures (Sanger).

With continued reference to FIG. 1, the preferred peptide sequences include (a) the Cys-to-Cys residues, (b) a residue immediately N-terminal to the Cys-to-Cys residues and (c) the residue immediately C-terminal to the Cys-to-Cys residues, and preferably all of the residues C-terminal to the Cys-to-Cys residues. These preferred sequences are indicated as sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

As seen, the ten sequences can be classed into two groups: one group (sequences SEQ ID NO:1, SEQ ID NO:2, SEQ ID NO:3, SEQ ID NO:4, SEQ ID NO:5 and SEQ ID NO:6 containing 14 Cys-to-Cys residues, and a second group (sequences SEQ ID NO:7, SEQ ID NO:8, SEQ ID NO:9, and SEQ ID NO:10 containing 19 Cys-to-Cys residues. The *P. aeruginosa* strains from which each sequence is derived are: SEQ ID NO:1, PAK; SEQ ID NO:2, PAK (Lys-to-Arg mutation); SEQ ID NO:3, PAO; SEQ ID NO:4, CD4; SEQ ID NO:5, KB7; SEQ ID NO:6, K122; SEQ ID NO:7, P1; SEQ ID NO:8, GA1 ; SEQ ID NO:9, 492C; and SEQ ID NO:10, TBOU1. The peptides are referred to herein by their strain designation. For example, a peptide containing the sequence SEQ ID NO:1 is referred to herein as the "PAK peptide", meaning the C-terminal, disulfide-linked peptide region of *P. aeruginosa* K pilin protein, having the additional constraints noted below.

Preferred disulfide-linked peptides also include amino acid variations of the given sequences which are internally consistent among sequences SEQ ID NO:1, SEQ ID NO:2, SEQ ID NO:3, SEQ ID NO:4, SEQ ID NO:5 and SEQ ID NO:6 and among sequences SEQ ID NO:7, SEQ ID NO:8, SEQ ID NO:9 and SEQ ID NO:10. Thus, for example, the first (left-hand) residue into the group of peptide SEQ ID NO:1, SEQ ID NO:2, SEQ ID NO:3, SEQ ID NO:4, SEQ ID NO:5 and SEQ ID NO:6 contains possible variations K, A, T, and S, and the third position in this group contains possible variations T, K, and A.

It is noted that the internal-variation substitutions are those substitutions found in nature, and thus are apparently compatible with requisite antigenic properties of the peptide. Further, the substitutions are generally within groups of amino acids having similar properties related to one or more of the following: (1) hydrophobicity; (2) polarity; (3) size of side chain; (4) charge; (5) preference for turns; (6) preference for beta strand secondary structure; and (7) preference for helical secondary structure. For example, at several positions, the allowed substitution variations is between T (Thr) and S (Ser), or between Y (Tyr) and F (Phe). The amino acid variation is also supported by the Ala-substitution effects discussed below.

In addition, the peptides are characterized by:

(a) a disulfide linkage between the two Cys (C) residues;

(b) immunospecific binding to PK99H or PK34C monoclonal antibody (Mab);

(c) specific binding to human buccal or human tracheal epithelial cells; and (d) absence of specific binding to *P. aeruginosa* pilin protein.

The disulfide link between the two Cys residues, which effectively cyclizes the peptide, has been found to be important for the immunogenicity of the peptide, when preparing anti-sera which are cross-reactive with pili from different *P. aeruginosa* strains (Lee), as will be discussed below.

The PK99H and PK34C Mab's are prepared against the PAK pili and are cross-reactive with various other *P. aeruginosa* strain pili, as will be seen below. The requirement that the peptide of the invention have crossreactivity with at least one of these antibodies ensures that the peptide has requisite epitopic similarity to the PAK peptide.

Also as will be seen below, the peptide of the invention has the ability to bind to a receptor site on human buccal epithelial cells (BECs) and human tracheal epithelial cells (TECs), and this binding is effective to inhibit *P. aeruginosa* binding to these epithelial cells. The requirement for peptide binding to these cells ensures that the peptide has the requisite receptor binding activity.

The absence of specific binding to *P. aeruginosa* pilin protein distinguishes the peptide from earlier reported C-terminal *P. aeruginosa* fragments (Paranchych) which contain the C-terminal sequences of the PAK strain peptide, but in addition, contain N-terminal residues which cause peptide binding to pilin protein. Such binding is presumably related to the self-aggregating property of the pilin protein. Such binding represents unwanted epitope(s) for the purposes of the present invention.

The peptides of the invention may contain additional N-terminal or C-terminal residues, consistent with the above constraints.

The effect of Ala substitutions at each of the 15 residue positions in the PAK peptide other than the two Cys residues was examined, to identify the region of the peptide most sensitive to amino acid variations. Briefly, peptides with specific Ala substitutions were compared with unsubstituted PAK peptide for binding affinity to anti-PAK monoclonal antibody PK99H (described below). The unsubstituted and substituted peptides were prepared by solid-phase synthesis, substantially as described in Example 1. Relative binding affinities of the unsubstituted and each of the substituted peptides was determined by competitive enzyme-linked immunosorbent assay (ELISA), according to standard procedures. Relative binding was expressed as $logIC_{50}$ (substituted)-$logIC_{50}$ (native), where $IC_{50}$ is the peptide concentration needed to displace 50% of an enzyme-linked peptide from immobilized antibody.

The results are shown in FIG. 2. A positive value of $logIC_{50}$ (substituted)-$logIC_{50}$ (native) indicates loss of binding affinity in the substituted peptide. As seen, the residue positions most sensitive to Ala substitution are positions 7 (Asp), 8 (Glu), 10 (Phe), 11 (Ile), 12 (Pro), and 13 (Lys). As seen in FIG. 1, these positions are highly conserved in the peptide sequences (i)–(vi), particularly at positions 7 (Asp and Glu), 10 (Phe and Tyr), 12 (Pro), and 13 (Lys and Asn).

Since residues 7–13 are most critical for binding activity, and substitution on either side of this region has relatively little effect on binding activity, it is seen that a peptide containing this 7-mer, and optionally, N-terminal or C-terminal flanking residues, may also be used for the peptide applications described below, including its use as a vaccine against *P. aeruginosa* and against bacterial and fungal bacterial and fungal organisms which have surface proteins which are antigenically crossreactive with antibodies produced against the C-terminal, disulfide-linked peptide region of *Pseudomonas aeruginosa* pilin protein.

The sequences of the 7mer peptide, and corresponding 17mer peptides derived from sequences SEQ ID NO:1, SEQ ID NO:2, SEQ ID NO:3, SEQ ID NO:4, SEQ ID NO:5 and SEQ ID NO:6 above are represented as SEQ ID NO:11, SEQ ID NO:12, SEQ ID NO:13, SEQ ID NO:14 and SEQ ID NO:15 below, respectively. As with sequences SEQ ID NO:1, SEQ ID NO:2, SEQ ID NO:3, SEQ ID NO:4, SEQ ID NO:5 and SEQ ID NO:6, the 7mer sequences include internal variations among the six sequences, and the peptide is further characterized by (a) immunospecific binding to PK99H or PK34C monoclonal antibody; and (b) absence of specific binding to *P. aeruginosa* pilin protein. The peptide may be flanked by disulfide-linked Cys groups, preferably spaced 1–5 residues from the N-terminal D or E residue of the 7mer, and 1–2 residues from the C-terminal Lys or Asn residue of the 7mer.

The *P. aeruginosa* strains from which each sequence is derived are: SEQ ID NO:11, PAK or, PAK (Lys-to-Arg mutation); SEQ ID NO:12, PAO; SEQ ID NO:13, CD4; SEQ ID NO:14, KB7; and SEQ ID NO:15, K122. These "core" peptides are referred to herein by their strain designation. For example, a peptide containing the sequence SEQ ID NO:1 is referred to herein as the "PAK core peptide", meaning the C-terminal, disulfide-linked peptide region of *P. aeruginosa* K pilin protein, having the 7 core residues and additional constraints noted above.

The binding of the PAK peptide (in both reduced and oxidized form) to BECs and TECs, and the ability of the peptide to inhibit pilin protein binding to TECs and BECs has been described in the earlier-filed co-pending application. Briefly, BEC and TEC preparations were made as described in Example 2. Binding of the PAK peptide to BECs was carried out by first successively contacting BECs with (a) the PAK peptide, (b) PK99H mouse monoclonal antibody (which binds immunospecifically to PAK peptide), and (c) enzyme-labeled goat anti-mouse antibody. The amount of peptide bound (expressed as measured enzyme activity) as a function of peptide concentration is shown in FIG. 3 for reduced (solid squares) and oxidized (+) peptide. Binding to the PAK peptide to TECs was similarly shown.

Figure 4:
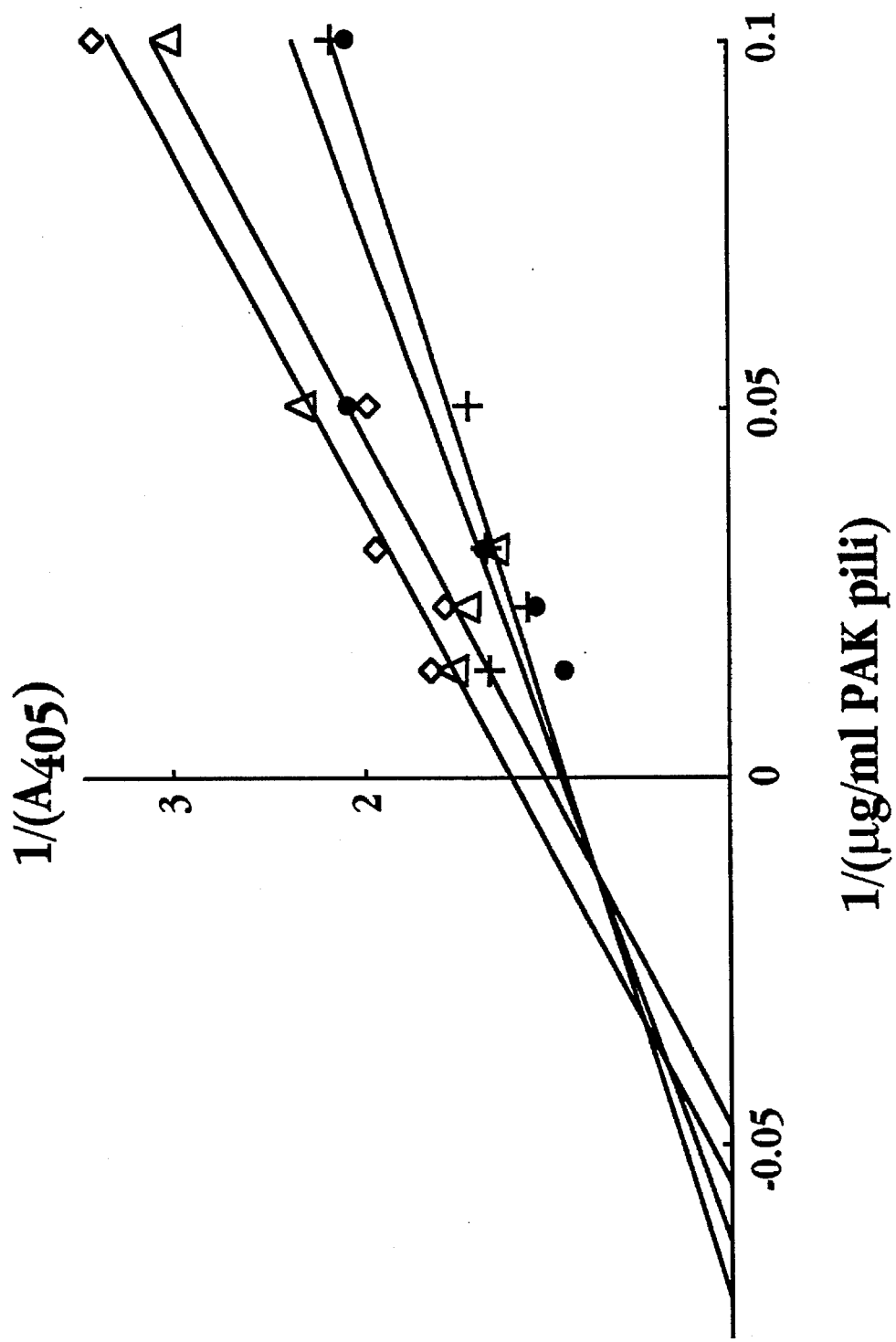
FIG. 4 is a modified Lineweaver-Burk plot of the binding of PAK pili to human BECs, showing inhibition of binding by increasing concentrations of PAK peptide.
Figure 8A:
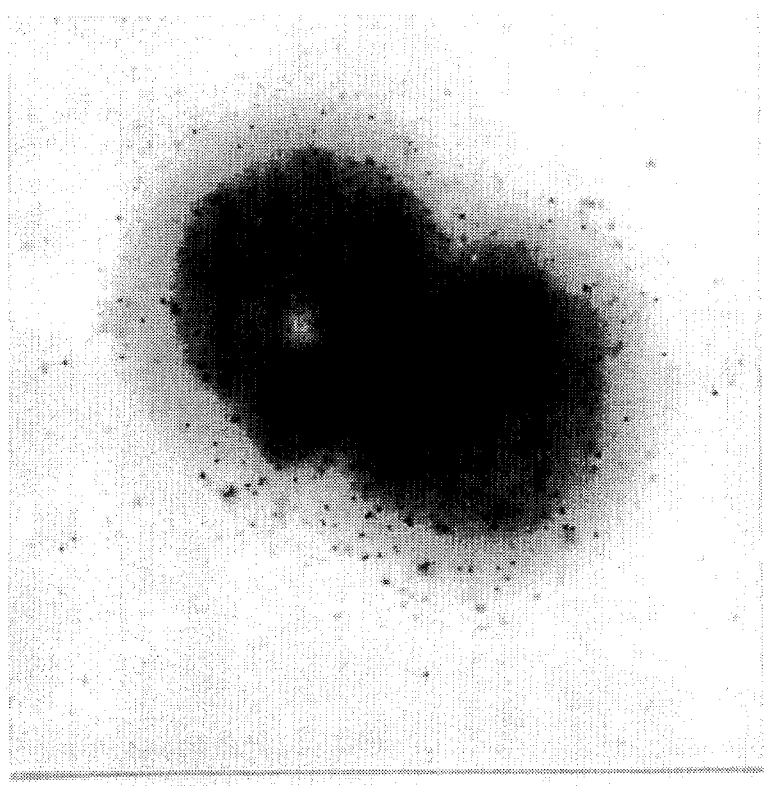
FIGS. 8A and 8B are immunoelectron micrographs showing M. catarrhalis cells after binding with polyclonal anti-PAK pili antibody (8A) and a control antibody (8B)
Figure 8B:
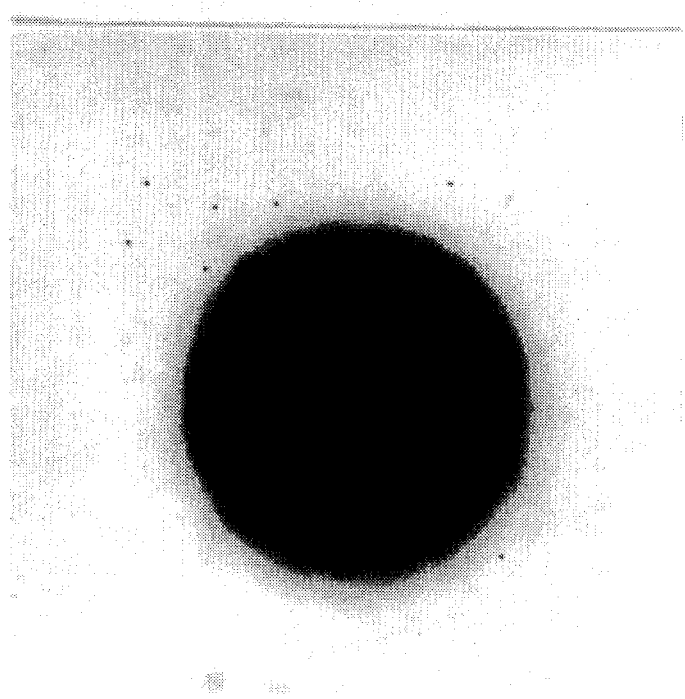
Figure 9A:
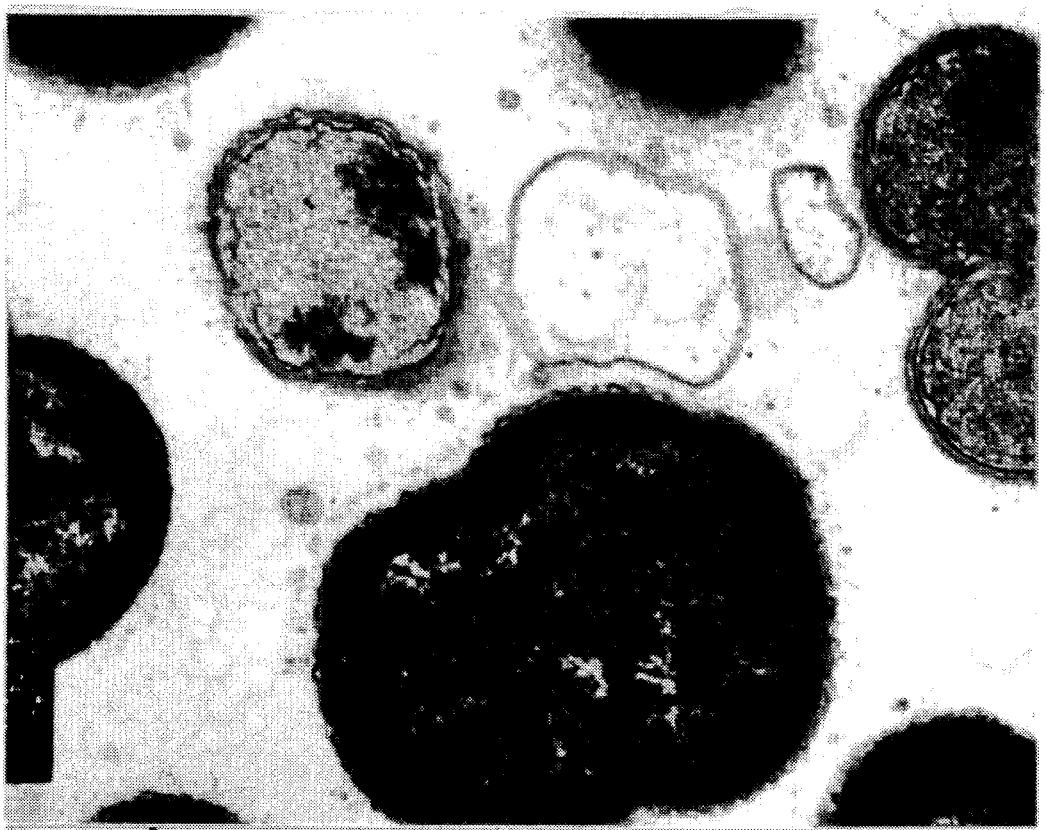
FIGS. 9A and 9B are electron micrographs showing M. catarrhalis bacteria with PK99H antibody localized by colloidal gold.
Figure 9B:
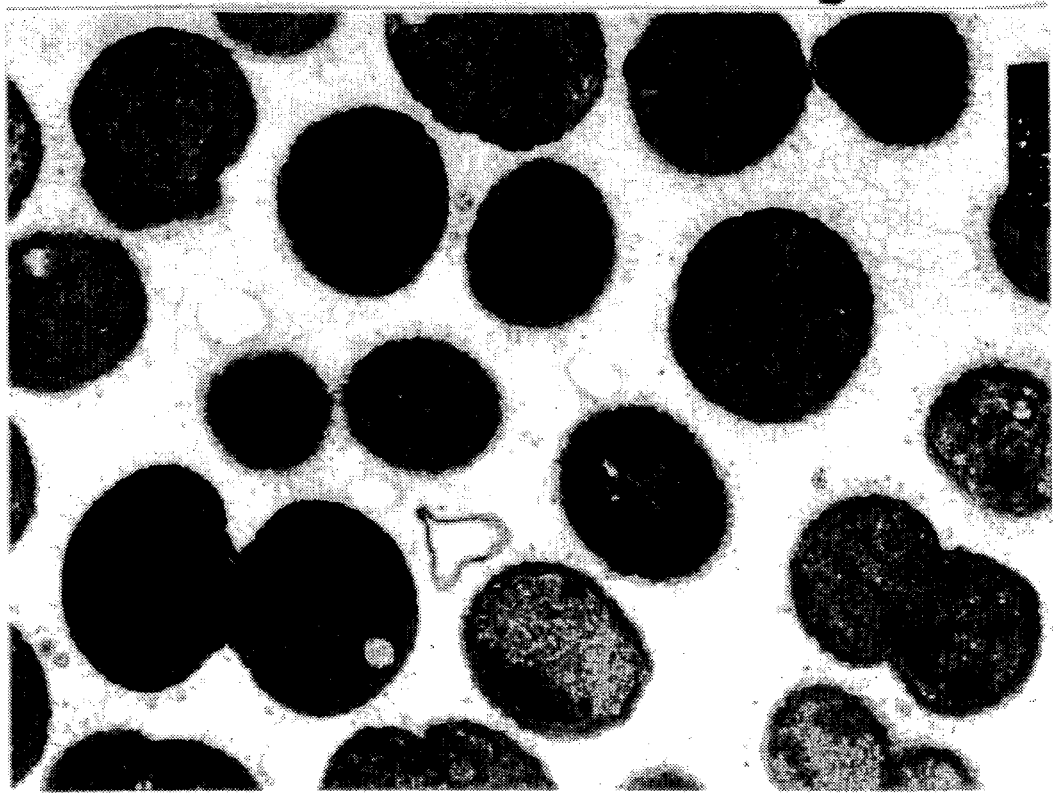

The ability of the PAK peptide to inhibit pilin protein binding to BECs was measured by competitive binding in which BECs were first incubated with one of a series of increasing concentrations of reduced-form PAK peptide, then with pilin protein, at one of a series of increasing concentrations. The amount of pilin protein bound to the cells was measured by contacting the cells successively with a PK3B mouse monoclonal antibody (which is immunospecific against pilin protein, but does not recognize the PAK peptide) and enzyme-labeled goat anti-mouse antibodies, then assaying enzyme activity bound to the cells. The results are plotted as a Lineweaver-Burke plot in FIG. 4, which shows the inverse of measured enzyme activity plotted as a function of the inverse of pili protein concentration, at 0 (X), 40 ($\overline{X}$), 80 (open triangles), and 120 (open diamonds) nmoles/ml of peptide. As seen, the peptide produced a concentration-dependent inhibition of pilin protein binding to BECs.

III. Anti-Peptide Antibodies

This section summarizes methods of production, and antibody binding characteristics of polyclonal and monoclonal antibodies which are immunoreactive with the peptides of the invention. The antibodies are useful in selecting random-sequence peptides having cross-reactivity with *P. aeruginosa* pilin C-terminal peptide, as detailed in Section V, and in preparing chimeric therapeutic antibodies, as detailed in Section VII.

IIIA. Polyclonal Antibodies

Polyclonal antibodies specific against reduced and oxidized forms of PAK peptide were prepared as described in the earlier-filed co-pending application, and as published (Lee). Briefly, PAK peptides were conjugated to keyhole limpet hemocyanin (KLH), and the conjugate was used to immunize female Flemish rabbits. The peptides include the PAK peptide in reduced ($PAK_{red}$) and oxidized form ($PAK_{ox}$) form, and PAK with an Ala substitution at the N-terminal Cys residue ($PAK_{Ala}$). Rabbits were given an initial immunization, two weeks later given a booster immunization, and then bled two weeks later. An immunoglobulin fraction was purified by Protein A affinity chromatography. Antibody binding to native PAK pilin protein, PAK peptide, and PAO peptide was examined by standard ELISA procedures (Worobec). Antibody specificities were as follows:

(a) The antisera produced by both $PAK_{ox}$ and $PAK_{red}$ was able to bind native PAK pili, and the titers raised against both peptides were similar;

(b) The antisera raised against the $PAK_{ox}$ peptide was strongly crossreactive with native PAO pili;

(c) The antisera raised against the $PAK_{red}$ peptide was only weakly crossreactive with native PAO pili; and (d) antisera prepared against the $PAK_{Ala}$ peptide did not bind to either PAK or PAO pili protein.

The results show that, although both oxidized and reduced forms of the peptide are effective to induce antibodies which are reactive with same-species pilin protein, the oxidized (disulfide-linked) form of the peptide is important for stimulating production of antibodies which are cross-reactive with pilin proteins from other *P. aeruginosa* strains.

The ability of the polyclonal antibodies to inhibit PAK pilin binding to BECs was examined, as detailed in Example 3. Briefly polyclonal antibodies were prepared against several peptide regions corresponding to the PAK peptide and from these, Fab fragments were prepared. The Fab fragment designations are ("r1," "r2") and ("o1" and "o2"), against the reduced (r) and oxidized (o) forms of PAK peptide (residues 128–144 of the PAK pilin protein); "22," against residues 22–33 (of the PAK pilin protein); "41," against residues 41–49; ≡58,☐ against residues 58–70; "75," against residues 75–84; "89," against residues 89–99; "107," against residues 107–116; and "117," against residues 117–125. "Pre" refers to preimmune sera; and "99H" to monoclonal antibody PK99H. The Fab fragments were preincubated with PAK pili before the addition of BECs, and the amount of pilin protein bound to the BECs was detected, as above, by successive binding of mouse monoclonal antibody PK3B (which is specific against pili protein, but not the PAK peptide), and enzyme-linked goat anti-mouse antibody. The results, expressed as percent inhibition of pili binding with respect to preimmune antibody Fab fragments, are shown in the bar graph of FIG. 5.

The bar graph demonstrates that Fab fragments produced against regions other than the C-terminal of PAK pilin are ineffective at preventing pilin binding to BECs. The most effective fragments are r1, r2, o1 and o2, directed against residues 128–144, reducing pili binding to 40% to 70% of the control and preimmune serum. This is similar to the effect shown by Fab 99H which is made from anti-PAK pilin monoclonal antibody PK99H (described below) which is also directed at this C-terminal region.

The studies with monoclonal antibodies, presented below, confirm that antibody inhibition of pilus binding to TEC or BEC cells also inhibits *P. aeruginosa* binding to these cells.

IIIB. Monoclonal Antibodies

Monoclonal antibodies against native PAK pili protein were prepared according to methods described elsewhere by the inventors (Doig). Briefly, BALB/c mice were immunized with weekly injections of PAK pili. Spleen cells from the animals were fused with mouse myeloma cell line NS1 (Irvin), and successful fusions were screened by an ELISA method for ability to secrete anti-pilin antibody. A library of 262 hybridoma clones that secreted antibodies immunoreactive with PAK pili were obtained. Protein A purified Mabs were then screened against pilin peptide fragments (Doig), to determine specificities of these antibodies. Four hybridoma cell lines were selected for further specificity studies: cell lines PK99H, PH34C, PK3B, and PK41C.

Immunoblots of purified PAK and PAO pili revealed that PK99H and PK3B Mabs were specific for PAK pilin protein, while PK34C and PK41C Mabs were immunoreactive with both PAK and PAO pilin peptide. PK99H and PK34C Mabs were both immunoreactive with a C-terminal fragment of PAK pilin.

Fab fragments prepared from PK99H and PK34C were examined for their ability to inhibit Pseudomonas pili binding to BECs, as detailed in Example 4B. Briefly, Fab fragments of PK99H, PK34C, and non-immune IgG were preincubated with PAK pili at the concentrations indicated in Table 1, followed by addition of BECs and further incubation at 37° C. for 2 hours. Binding to the BECs was detected by an ELISA method, with the results shown in Table 1.

TABLE 1

| Fab Fragment | Concentration* (μg/ml) | % of Control |
| --- | --- | --- |
| PK99H | 100 | 53.5 ± 3.3 |
| PK99H | 200 | 7.5 ± 0.6 |
| PK34C | 100 | 44.5 ± 0.1 |
| PK34C | 200 | 4.5 ± 0.7 |
| IgG** | 100 | 95.6 ± 0.9 |
| IgG | 200 | 94.9 ± 2.2 |

*Final Concentration of Fab fragments. The final concentration of PAK pilii used was 5 μg/ml.
**Fab fragments prepared from normal mouse IgG.

As seen, both PK99H and PK34C Fab fragments produced a concentration-dependent inhibition of pili binding to BECs. Non-immune IgG Fab fragments produced only a slight decrease in pili binding.

Figure 6:
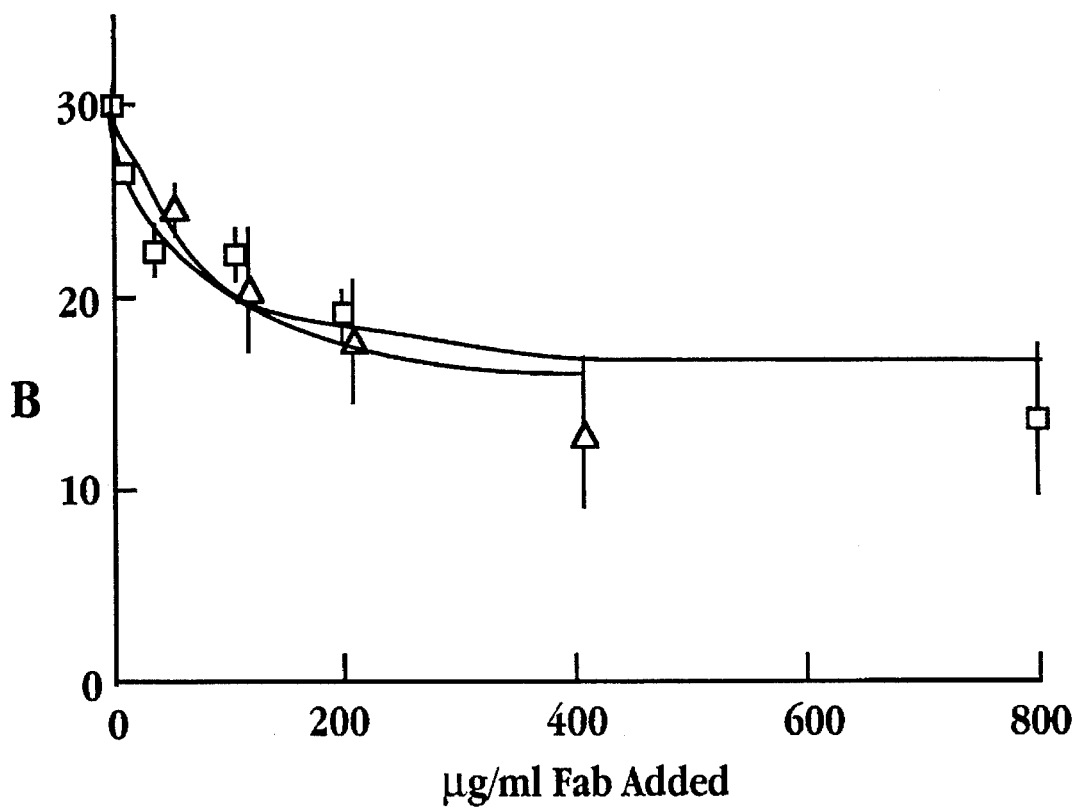
FIG. 6 is a plot showing the inhibition of Pseudomonas bacteria binding to BECs by Fab fragments of monoclonal antibodies PK99H (open squares) and PK34C (open triangles)

The ability of Fab fragments of PK99H and PK34C to block binding of a number of different *P. aeruginosa* strains (Table 2) to BECs was also investigated. The bacterial strains were first incubated with the Fab fragments, then mixed with BECs. Binding of the bacteria to the cells was performed as described (McEarchran). FIG. 6 shows the inhibition of *P. aeruginosa* K binding to BECs, as a function of antibody Fab concentration. The Fab fragments were prepared from the monoclonal antibodies PK99H (open squares) and PK34C (open triangles). As seen, both antibody fragments are effective in inhibiting *P. aeruginosa* binding to target epithelial cells.

The effect of the PK99H, PK34C, and non-immune control IgG Fab fragments binding of the different Pseudomonas strains is given in Table 2.

TABLE 2

| | Bacteria bound/BEC<sup>a</sup> | | |
| --- | --- | --- | --- |
| Strain | Control<sup>b</sup> | PK99H | PK34C |
| PAK | 35.2 ± 1.4 | 25.6 (72.7) ± 1.0 | 23.8 (67.5) ± 1.70 |
| PAO | 50.5 ± 2.0 | 55.5 (110) ± 11.1 | 45.9 (91) ± 0.7 |
| HD1 | 38.0 ± 3.6 | 31.0 (81.6) ± 3.5 | 31.3 (82.5) ± 1.1 |
| 492c | 30.9 ± 0.2 | 23.8 (77.1) ± 0.5<sup>c</sup> | 26.2 (84.4) ± 1.4 |
| P1 | 36.3 ± 2.5 | 34.7 (95.6) ± 5.9 | 29.5 (81.3) ± 0.2 |
| K122-4 | 41.8 ± 1.5 | 38.3 (91.8) ± 2.8 | 28.0 (67.1) ± 0.4 |
| PAK/3 | 13.1 ± 1.4 | 12.0 (91.9) ± 0.7 | 12.1 (93.3) ± 0.6 |

<sup>a</sup>The concentration of PK99H and PK34C Fab used in the inhibition assay was 100 μg/ml and had a titer of 10⁵ by ELISA, using PAK pili as the antigen (coated at 1 μg per well). Given is the mean ± the standard deviation. The percent of control is given in parentheses.
<sup>b</sup>Control value when 100 μg of Fab fragments per ml produced from normal mouse IgG was added. No difference was noted between these values and those from tubes to which no Fab fragments were added.
<sup>c</sup>The significant difference (P <0.05) was determined by using the Student t test.

The data show that the PK99H antibody produces binding inhibition of binding of strains PAK, HD1, and 492c. The PK34C antibody, by contrast, produces a significant inhibition of binding of all of the strains tested except PAK/3. The results indicate that the PK34C antibody is more crossreactive, among Pseudomonas strains, than the PK99H antibody. The data also demonstrate that antibodies effective in inhibiting Pseudomonas binding to BECs are also effective in inhibiting Pseudomonas bacterial attachment to BECs.

IV. Inhibiting Bacterial and Fungal Infections

As demonstrated above, antibodies produced against the C-terminal disulfide-linked peptide region of *P. aeruginosa* K pilin protein, such as monoclonal antibody PH34C, are immunoreactive with pilin protein from a variety of *P. aeruginosa* strains, as evidenced by the ability of the antibody to block binding of different Psuedomonas strains to BECs.

In accordance with one aspect of the invention, it has been discovered that antibodies produced against the C-terminal, disulfide-linked peptide region of *P. aeruginosa* are crossreactive with surface proteins on a variety of bacterial and fungal microorganisms. Antibody binding to bacterial and fungal proteins and/or cells are presented below. Additional studies on the ability of the antibodies to inhibit *Candida albicans* binding to BECs, also presented below, demonstrate that such binding is effective to inhibit cell binding to target epithelial cells, such as BECs.

The invention thus includes, in another aspect, a method of blocking attachment to target epithelial cells, of bacterial and fungal organisms which have surface proteins which are antigenically crossreactive with antibodies produced against the C-terminal, disulfide-linked peptide region of *Pseudomonas aeruginosa* pilin protein. The method includes contacting the bacterial or fungal microorganism with such antibodies produced against the C-terminal, disulfide-linked peptide region of *P. aeruginosa*, to bind to the crossreactive surface protein. This binding is then effective to block binding of the microorganism with target epithelial cells, such as TECs and BECs.

The peptide used to produce the antibody is preferably selected from the peptide disclosed in Section II, including a peptide selected from the group of peptides identified as SEQ ID NO:1, SEQ ID NO:2, SEQ ID NO:3, SEQ ID NO:4, SEQ ID NO:5 and SEQ ID NO:6, SEQ ID NO:7, SEQ ID NO:8, SEQ ID NO:9 and SEQ ID NO:10, and SEQ ID NO:11, SEQ ID NO:12, SEQ ID NO:13, SEQ ID NO:14 and SEQ ID NO:15. Alternatively, the peptide used to produce the antibody is one selected for its cross-reactivity with *P. aeruginosa*, as described in Section V.

The antibody, either a polyclonal or monoclonal, may be generated by standard methods, such as those outlined in Section III. One antibody useful in the method is the PK99H or the PK34C monoclonal antibody described in Section III. For therapeutic purposes, i.e., where the antibody is administered parenterally, the antibody is preferably a chimeric antibody containing the variable region of a mouse monoclonal antibody, such as antibody PK99H or PK34C, and the constant region of a human immunoglobulin gene. Details of preparing such an chimeric antibody of this type are given in Section VII below. Alternatively, the antibody may be produced by vaccination with a C-terminal *P. aeruginosa* peptide, as described in Section VI.

IVA. *Moraxella catarrhalis*

*Moraxella catarrhalis* produces two morphological forms of pili (Marrs) and binds to human respiratory epithelial cells (Carr). It has been suggested (Marrs) that at least one of the pili produced is an N-methylphenyl alanine (N-MePhe) pilus, the same class of pili that is produced by Neisseria, *P. aeruginosa*, *Moraxella bovis*, *Bacteroides nodosus*, and *Vibrio cholerae* (Paranchych, 1988) based on agar corrosion, twitching motility, and probing with a *M. bovis* pilin gene probe.

Experiments conducted in support of the present invention have confirmed the earlier observations (Marrs) that *M. catarrhalis* produces two morphological forms of pili, designated alpha and beta pili. Further studies in support of the invention have shown that a 1.2 kb HindIII *P. aeruginosa* PAK pilin gene probe hybridizes with reasonable stringency to restriction endonuclease fragments of a number of *M.*

*catarrhalis* clinical isolates. Additional studies have established that rabbit polyclonal anti-Pseudomonas PAK pili antisera (Section III above) reacts specifically with an 18 kD protein (lane 2 in FIG. 7) in immunoblots. This 18 kD protein constitutes the structural subunit of the beta pili.

The beta pilus type is significantly associated with virulence in *M. catarrhalis*, being found with high frequency in virulent strains in a retrospective epidemiological study. In one study, the distribution of alpha and beta pili types among 43 clinical isolated of colonized and infected patients showed, for alpha pili, 67% and 87% in colonized and infected patients, respectively, and for beta pili, 42% and 81% in colonized and infected pili, respectively. The immunolocalization study described in Example 5 shows that polyclonal anti-PAO pili antisera binds with high affinity to the surface and surface appendages of *M. catarrhalis*.

IVB. *Porphyromonas gingivalis*

Figures 7, 10:
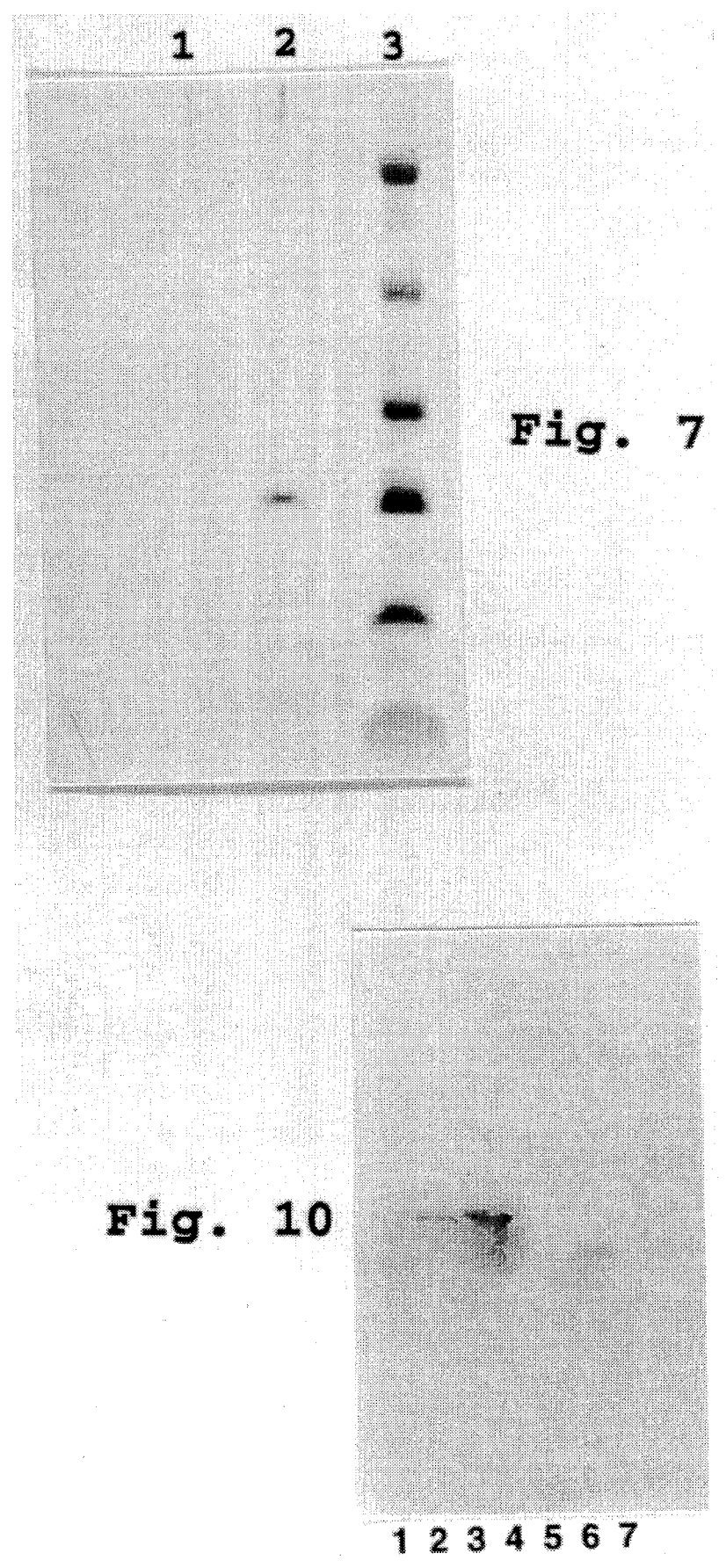

Monoclonal antibody PK99H was found to cross-react with a *Porphyromonas* (previously referred to as Bacterioides) *gingivalis* 40 kD cellular protein in a number of isolates (obtained from Dr. R. Ellen, Faculty of Dentistry, University of Toronto, Toronto, Ontario) on the basis of an immunoblot. Briefly, total cellular protein of *P. gingivalis* colonies cultured anaerobically in an anaerobe jar on BHI agar was solubilized, separated by SDS-PAGE, electrophoretically transferred onto nitrocellulose, and immunoblotted with monoclonal antibodies PK99H and PK34C as previously described. PK99H was observed to bind specifically to a 40–50 kD protein depending on the isolate, as seen in FIG. 10. The legend for the Western blot is as follows:
1. *Bacteroides intermedius*, ATCC 25611
2. *Bacteroides intermedius*, NTCC 9336
3. *Porphyromonas* (Bacteroides) *gingivalis* 381
4. *Porphyromonas gingivalis* 9–14k-1
5. *Bacteroides melaninogenicus* 20/30
6. *Porphyromonas gingivalis* 33277
7. *Bacteroides melaninogenicus* VPI 2381

The lack of reaction with bacteria other than *P. gingivalis*, and the weak reaction with *B. intermedius* NTCC 9336 may be due to low pilus expression by the other strains, rather than lack of reactivity with the PK99H antibody.

IVC. *Candida albicans*

Figure 11:
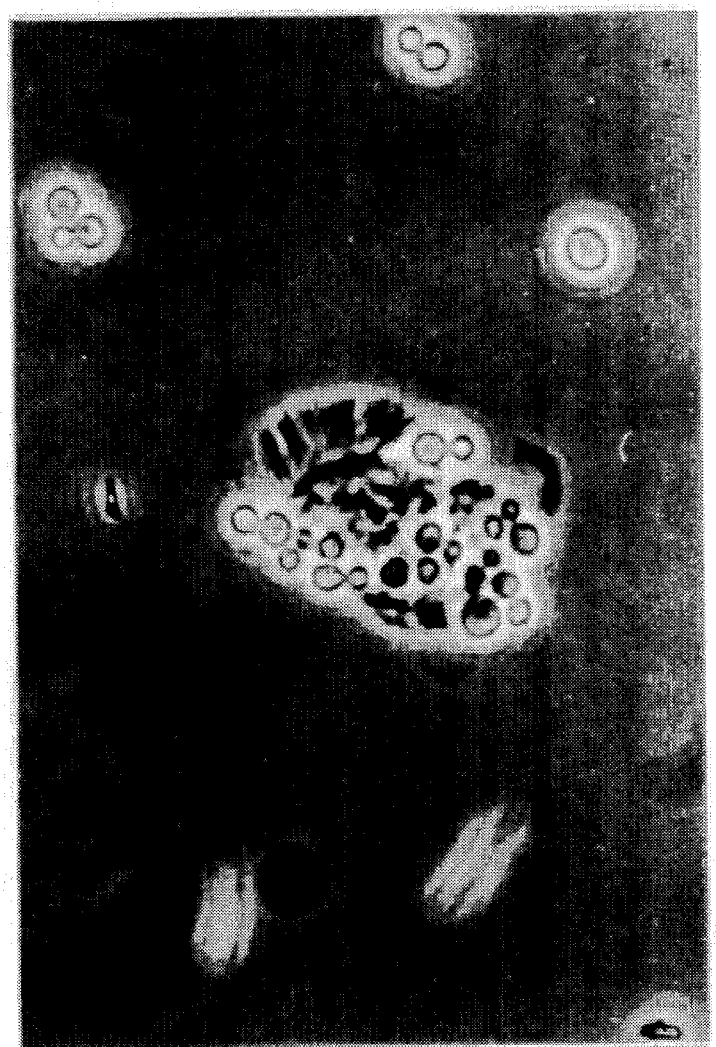
FIG. 11 is a phase contrast micrograph of Candida cells bound to BECs.

The binding of *C. albicans* to TECs and BECs was examined in studies on inhibition of fungal cell attachment to target epithelial cells. Several *C. albicans* strains identified in Example 6A were used. BECs and TECs were obtained as described in Example 6B and 6C, respectively. The binding to *C. albicans* cells to TECs and BECs can be shown by microscopic methods, such as described in Example 6D. FIG. 11 is a phase-contrast photomicrograph showing *C. albicans* cells (light cells) bound to TECs (dark cells). Quantitative binding of *C. albicans* cells to BECs and TECs was also demonstrated by the adhesion assay detailed in Example 6E.

Figure 12:
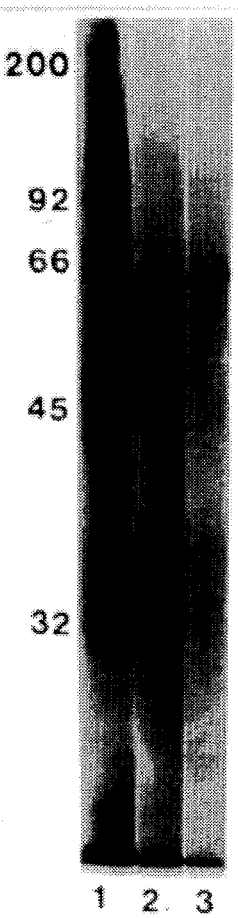
FIG. 12 shows SDS-PAGE gel patterns of purified Candida fimbrial protein (lane 3)

The adhesion protein in *C. albicans* is a fimbrial protein which forms surface self-polymerized fimbriae on the cell surface of the yeast cells. Fimbriae were obtained in substantially purified form by the isolation method detailed in Example 6F. Fractionation of purified fimbriae by sodium dodecylsulfate polyacrylamide gel electrophoresis (SDS-PAGE) gave the single 64 kD protein shown by silver staining in lane 3 of FIG. 12. The purified fimbriae consists of about 15% (w/w) protein and 85% carbohydrate (w/w) on the basis of colorometric assays.

Figure 13:
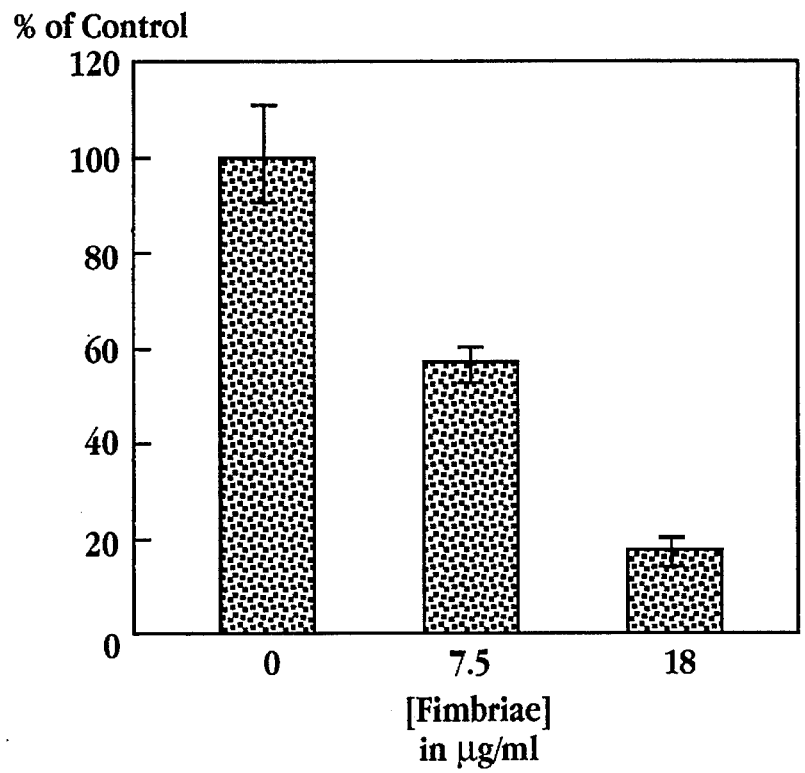
FIG. 13 is a bar graph showing the inhibition by Candida fimbriae on Candida adherence to BECs.

The ability of purified fimbriae to inhibit Candida attachment to BECs was studied by a direct competition method, as outlined in Example 6H. The results, given in the bar graph in FIG. 13, show that increasing concentrations of fimbriae produce increasing inhibition of Candida binding to the epithelial cells. These findings are consistent with the role of Candida fimbrial protein in fungal cell attachment to target epithelial cells.

Figure 14:
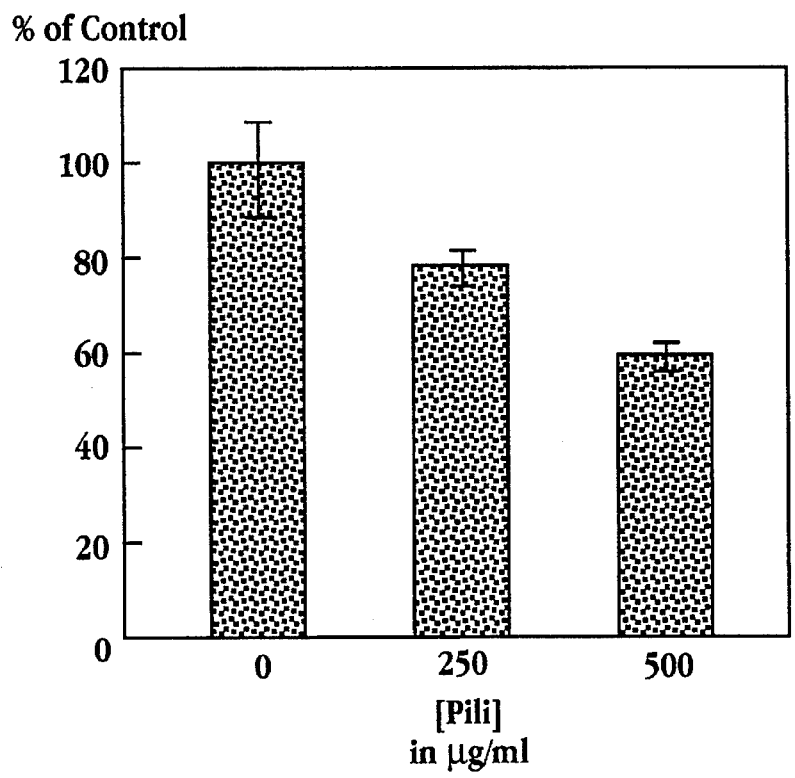
FIG. 14 is a bar graph showing the inhibition by Pseudomonas pili on Candida adherence to BECs.
Figure 15:
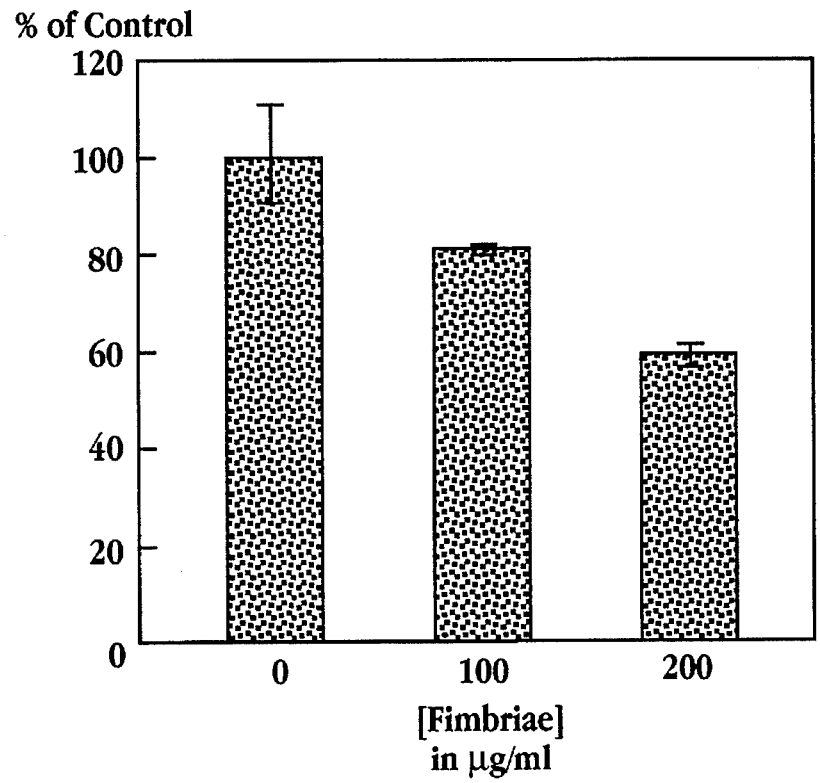
FIG. 15 is a bar graph showing the inhibition by Candida fimbriae on Pseudomonas pili binding to BECs.

Similar competitive inhibition studies were carried out with purified *P. aeruginosa* K pili, with the results shown in the bar graph of FIG. 14. As seen, relatively high concentrations of PAK pilin protein inhibited Candida binding to BECs in a concentration-dependent manner. Results of the reciprocal study, showing inhibition by Candida fimbriae protein of Pseudomonas pilin protein binding to BECs, are shown in FIG. 15.

The inhibition results just discussed indicate that attachment of both Pseudomonas cells through pili, and Candida cells through fimbriae, occur at a common epithelial cell receptor which is at least partially blocked by either the pilin or fimbrial protein.

These results, like the results obtained above for surface proteins from Pseudomonas, Moraxella, and Bacteroides bacterial cells, suggest a conservation of antigenic epitopes between Pseudomonas C-terminal pili peptide and fungal cell proteins. This conservation of sites is demonstrated by reciprocal competitive ELISA studies on pilin and fimbrial proteins for binding to antibodies specific against the C-terminal pilin peptide (PK99H and PK34C Mabs) and an antibody specific against fimbrial protein. The latter antibody is a polyclonal antibody prepared against purified fimbriae.

Details of the binding method are given in Examples 7A and 7B. Briefly, fimbrial or pilin protein were immobilized on a solid support. The competitor antigen and antibody are mixed together, then added to the solid support, at an antibody concentration such that about 50% of the immobilized antigen would be bound to the antibody, in the absence of the competitor. The amount of antibody actually bound to the solid support was determined by a standard ELISA method. The results of the study are given in Table 3 below. The similar binding affinity values of each of the three antibodies for the two different antigens indicates a strong conservation of epitopic sites between the two antigens.

TABLE 3

| Competitor | Fim Fim | Fim Pili | Pili Fim | Pili Pili |
|---|---|---|---|---|
| Antibody | | | | |
| PK99H | $1.21 \times 10^6$ | $2.04 \times 10^2$ | $1.84 \times 10^2$ | $3.0 \times 10^2$ |
| PK34C | $1.50 \times 10^5$ | $3.16 \times 10^2$ | $2.82 \times 10^2$ | $3.8 \times 10^2$ |
| Anti-Fim | $4.74 \times 10^1$ | $2.50 \times 10^1$ | $1.24 \times 10^2$ | $3.9 \times 10^1$ |

In a related study, rabbit polyclonal antibodies prepared against the PAK peptide in oxidized or reduced form were examined for binding affinity to the fimbrial and pili proteins. Antibody was added to the immobilized antigen, either pilin or fimbrial protein, at one of the 4 antibody dilutions shown at the left in Table 4. The amount of antibody bound to the support was assayed by the above ELISA method, with the results given in Table 4. Each polyclonal antibody against the C-terminal, disulfide-linked pili proteins showed high affinity for both pilin and fimbrial protein, again demonstrating a high conservation of epitopes between the two proteins.

TABLE 4

| | Anti-Oxidized Ab | | Anti-Reduced Ab | |
|---|---|---|---|---|
| | Antigen Immobilized | | | |
| Dilution | Fim | Pili | Fim | Pili |
| $10^{-1}$ | >2.0[1] | >2.0 | >2.0 | >2.0 |
| $10^{-2}$ | >2.0 | >2.0 | >2.0 | >2.0 |
| $10^{-4}$ | 0.450 | >2.0 | 0.598 | >2.0 |
| $10^{-6}$ | 0.430 | 0.496 | 0.480 | 1.28 |

1. The values are ELISA $A_{405}$ values.

The ability of the monoclonal antibodies PK99H and PK34C to cross react with a variety of C. albicans strains was examined by dot blotting, according to the method described in Example 7C. Briefly, cells of a selected Candida strain were immobilized on a nitrocellulose filter, and exposed successively to the PK99H or PK34C antibody, and goat anti-mouse antibody conjugated to alkaline phosphatase. The amount of antibody bound was measured by color change of a nitro blue tetrazolium substrate. The antibody levels measured are given in Table 5 below. It is evident from the results that all of the Candida strains were highly immunoreactive with the two anti-pili antibodies.

TABLE 5

| Candida Strain No. | PK99H | PK34C |
|---|---|---|
| 1 | $10^4$ | $10^2$ |
| 2 | $10^4$ | $10^4$ |
| 3 | $5 \times 10^4$ | $10^3$ |
| 4 | $5 \times 10^4$ | $10^3$ |
| 5 | $5 \times 10^4$ | $10^3$ |
| 6 | $5 \times 10^4$ | $10^6$ |
| 7 | $10^4$ | $10^4$ |
| 8 | $10^3$ | $10^5$ |
| 9 | $10^2$ | $10^4$ |
| 11 | $5 \times 10^4$ | $10^6$ |
| 12 | $5 \times 10^3$ | $10^6$ |
| 13 | $5 \times 10^4$ | $10^5$ |
| 14 | $5 \times 10^4$ | $10^5$ |
| 15 | $5 \times 10^4$ | $10^2$ |
| 16 | $10^4$ | $10^5$ |
| 17 | $10^4$ | $10^6$ |
| 18 | $10^4$ | $10^3$ |
| 19 | $5 \times 10^4$ | $10^3$ |
| #10 | $10^3$ | $10^3$ |
| #30 | $5 \times 10^4$ | $10^3$ |

Immunospecific binding of PK99H, PK34C, and of polyclonal anti-fimbrial antibody has also been demonstrated by indirect immuofluoresecence, after antibody binding to Candida cells.

Figure 16:
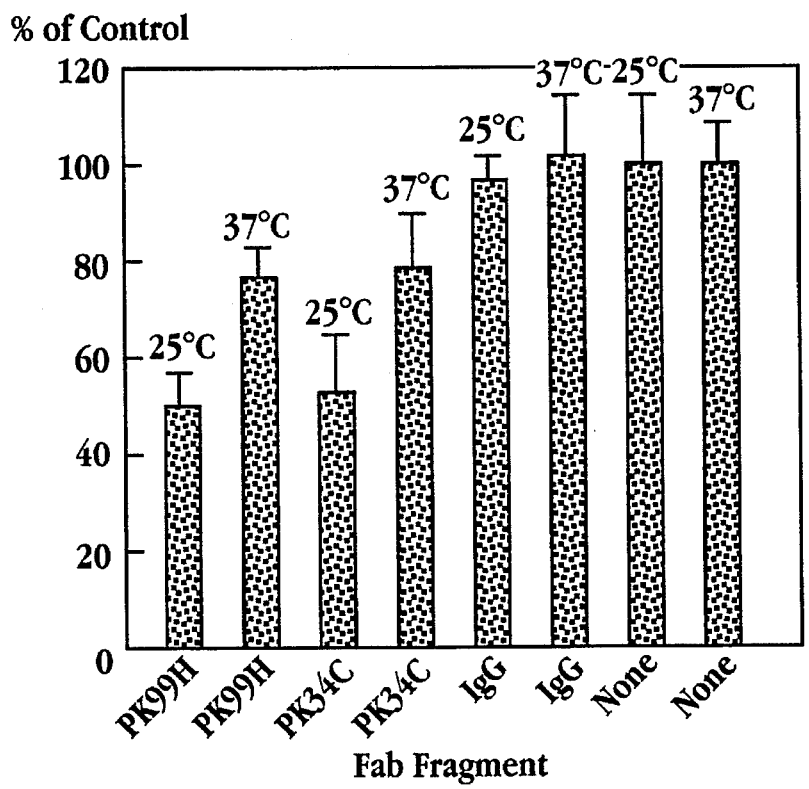
FIG. 16 is a bar graph showing the inhibition by anti-PAK pili antibodies on Candida binding to BECs.

The apparent common binding receptors for Pseudomonas pili and Candida fimbria and the conservation of epitopes between the two proteins indicate that the anti-Pseudomonas antibodies would be effective in blocking fungal cell binding to target epithelial cells. This effect has in fact been observed with the PK34C and PK99H antibodies. FIG. 16 shows the percent inhibition of Candida binding to BECs after initial exposure of the fungal cells to the antibody indicated. Details of the inhibition method are given in Example 7D. Significant inhibition was seen with both antibodies which are specific against Pseudomonas pilin protein C-terminal sequence.

It will be appreciated from the foregoing that a variety of bacterial and fungal cells have surface proteins which are immunoreactive with antibodies prepared against the Pseudomonas C-terminal pili peptide of the invention. Since binding of these cells to target epithelial cells is inhibited by antibodies prepared against the C-terminal pili peptide, such antibodies and vaccines for their production can be used to prevent and treat infection by the crossreactive microorganisms.

Bacteria and fungi which are responsive to such treatment can be readily identified by the methods described above, for example, by showing binding of antibodies prepared against Pseodomonas pili C-terminal peptide to the microorganism, or by showing crossreactivity of isolated adhesins to the antibodies.

V. Random-Sequence Antigens

The studies described above demonstrate that an antibody produced against the C-terminal pili peptide of the invention is specific against an epitope present in Pseodomonas pili as well as surface protein present in unrelated bacterial and fungal microorganisms. This finding can be exploited, in accordance with another aspect of the invention, for producing a generalized, random-sequence peptide which contains the epitope common to the different surface proteins. Such a generalized peptide has use in a vaccine composition, for provoking antibodies agaisnt the common epitope (Section VI), for preparing chimeric antibodies (Section VII), and for therapeutic use in a peptide aerosol method of treatment (Section VIII).

Methods for generating and identifying generalized, random-sequence peptides having a selected epitopic site have been reported recently (Scott; Cwirla). Both studies demonstrate that a large population of random-sequence peptides containing random-sequence peptides of 5–10 residues in length can be successfully screened, by immunospecific binding to a selected antibody (or other receptor) for the presence of peptides having a selected binding activity with respect to the receptor molecule. This method is thus effective to generate and identify novel sequences which are predicted to be alternate immunogens for generation of immunity against P. aeruginosa and other microbial species having a common immunoreactive site.

Example 8 describes a method by which random sequence peptides can be prepared and selected for usefulness as immunogens according to the invention. In the preferred method, approximately $10^7$–$10^8$ novel heptapeptides are generated through construction of an epitope library using the filamentous phage fUSE5 as a vector. Other filamentous phage vectors are considered to be equally efficacious in developing such a library. Alternatively, similar epitopic libraries can be generated in bacterial expression systems or in mechanically generated peptide systems (Geyson et al. CIBA Foundation Symp. 119: 131–149).

Figure 17:
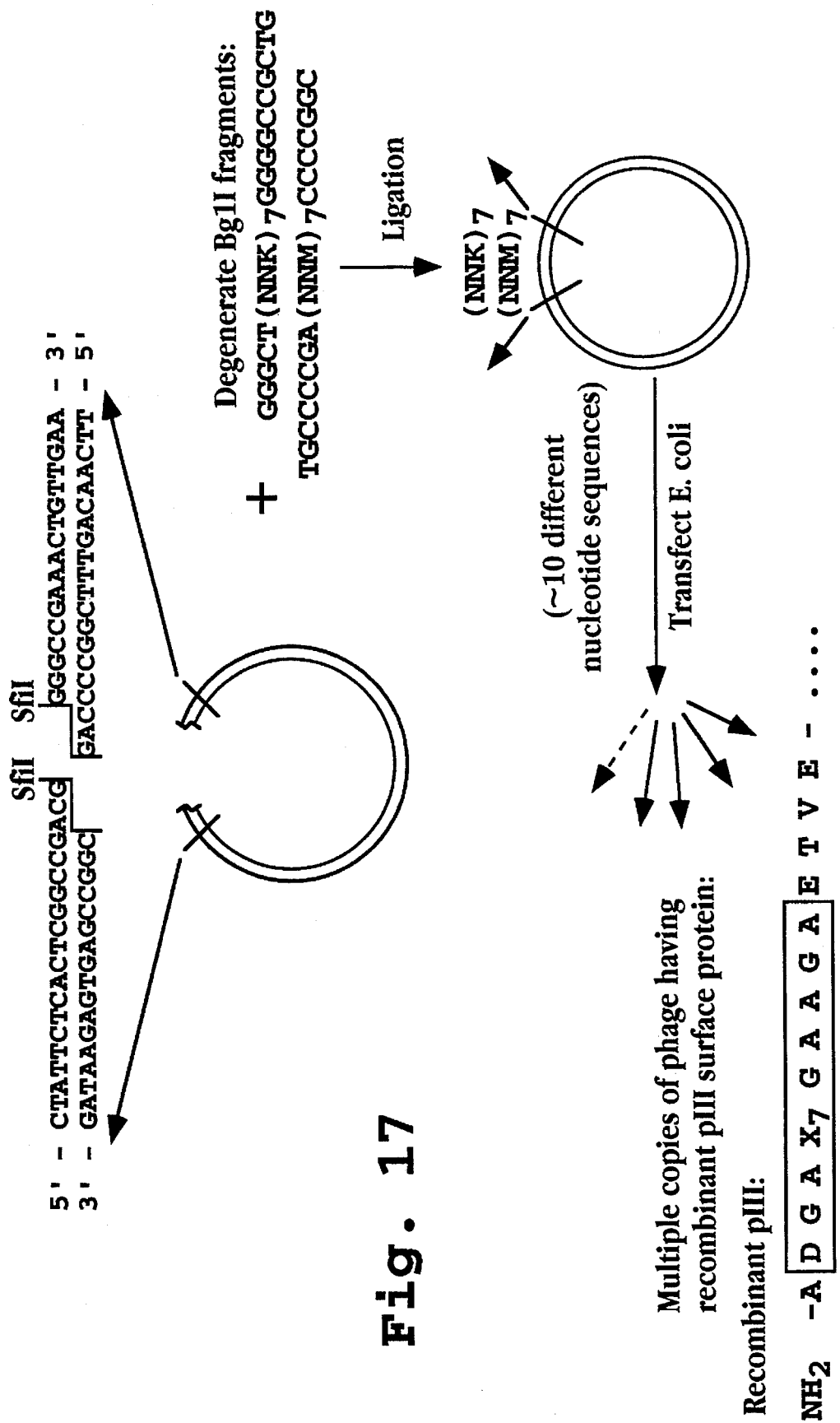
FIG. 17 illustrates recombinant methods for producing and selecting random-sequence peptides, in accordance with the invention.
Figure 17:
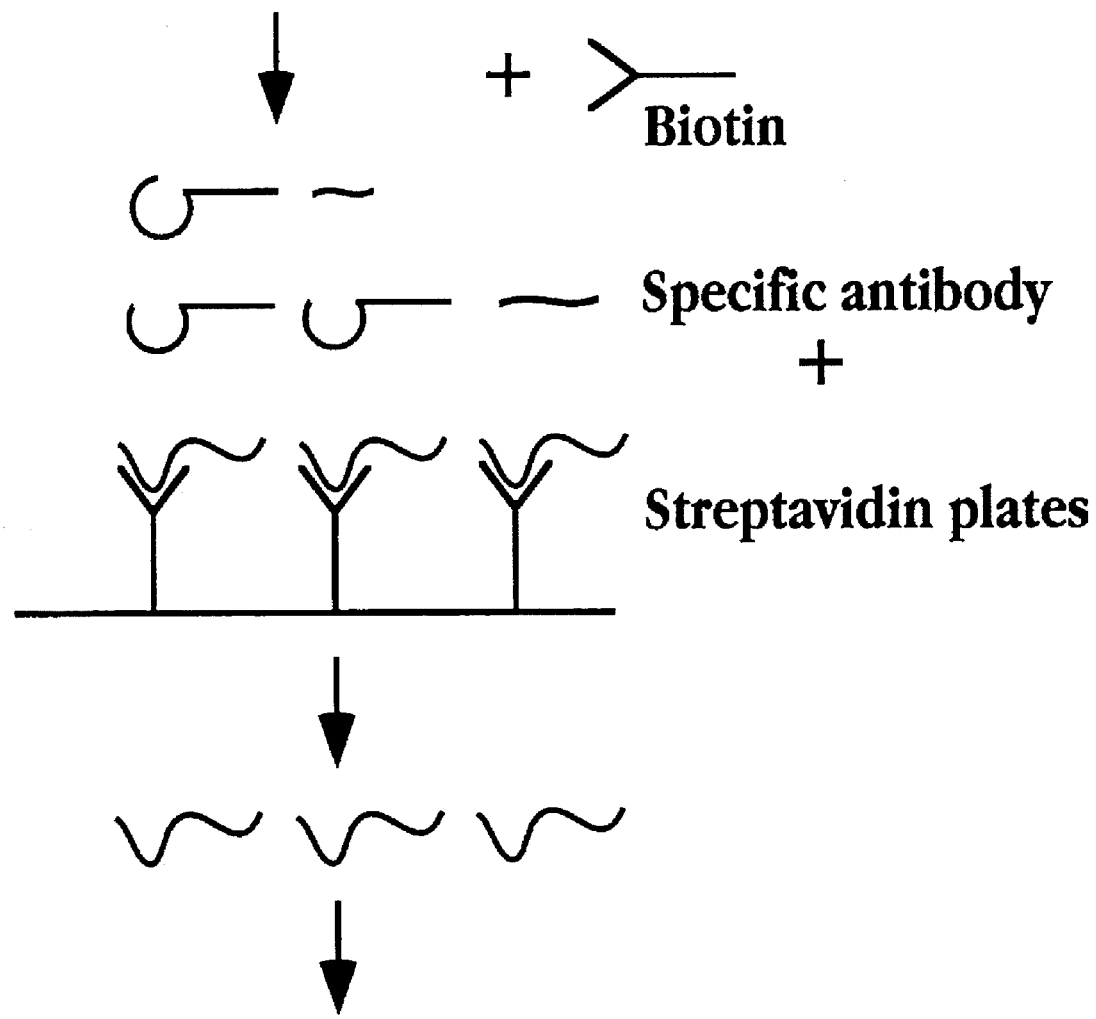

FIG. 17 shows schematically the sequence of steps necessary to generate and screen a fUSE5 filamentous phage epitopic library. Briefly, fUSE5 RF DNA is subjected to digestion with restriction endonuclease SfiI to create an insertion site for insertion of foreign DNA. A synthetic (15+3m) base pair (bp) BglI DNA fragment is prepared which contains a degenerate sequence of the form (NNK)m, where N represents A, G, C, or T; K represents G or T; and m can vary from 2 to 15. In the preferred embodiment of the invention, m ranges from 5–10, typically 6–7, and the bases are randomly added in single addition events to the template primer. An alternative method of achieving random addition of codons coding for the twenty amino acids is to randomly attach trinucleotide codons representing each amino acid to the template primer.

Following ligation of the insert to the cloning vector, amplification of the filamentous phage vector is achieved by transfection of E. coli cells. Successful transfection is measured by the presence of vector borne markers. In the preferred embodiment of the invention, this marker is tetracycline resistance. Recombinant phage are then isolated from bacterial cells. Phage bearing sequences of interest are isolated by an antibody panning method in which phage are incubated with the antibody of interest, e.g., PK34C or PK99H. Biotinylated second antibody (goat anti-mouse IgG) is then added, and complexes containing biotinylated second antibody, antibody PK34C or PK99H, and immunoreactive peptide bearing phage are separated from unreacted antibodies and phage by adhesion onto a streptavidin coated plate. After eluting phage-bearing immunoreactive sequences, the corresponding DNA coding sequences are determined.

The coding sequences corresponding to the selected-epitope peptide(s) are exploited using conventional peptide synthesis methods to produce the epitopic peptide. This may involve solid-phase synthesis, as described in Example 1, or recombinant peptide expressiion according to known methods.

Foreign DNA sequences present in the filamentous phage fusion protein pIII determine the sequence of the immunoreactive peptide. Peptides discovered to be immunoreactive through this procedure can then be synthesized by standard peptide synthetic methods and prepared as immunogens by conjugation to an appropriate peptide carrier.

VI. Vaccine Compositions

Also included in the invention is a vaccine composition containing a C-terminal Pseudomonas pili peptide and an immunogenic peptide carrier to which the peptide is bound. The composition is used as a vaccine against infection by bacterial and fungal organisms which have surface proteins which are antigenically crossreactive with antibodies produced against the C-terminal, disulfide-linked peptide region of P. aeruginosa pilin protein.

In one embodiment, the peptide includes the sequence represented as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. Including amino acid variations which are internally consistent among sequences SEQ ID NO:1, SEQ ID NO:2, SEQ ID NO:3, SEQ ID NO:4, SEQ ID NO:5 and SEQ ID NO:6 and among sequences SEQ ID NO:7, SEQ ID NO:8, SEQ ID NO:9 and SEQ ID NO:10. The peptide is further and characterized by: (a) a disulfide linkage between the Cys (C) residues and (b) immunospecific binding to a PK99H or a PK34C monoclonal antibody.

In another embodiment, the peptide includes the sequence represented as SEQ ID NO:11, SEQ ID NO:12, SEQ ID NO:13, SEQ ID NO:14, and SEQ ID NO:15. Including amino acid variations which are internally consistent among sequences SEQ ID NO:11, SEQ ID NO:12, SEQ ID NO:13, SEQ ID NO:14 and SEQ ID NO:15. The peptide is further characterized by: (a) immunospecific binding to a PK99H or a PK34C monoclonal antibody; (b) specific binding to human buccal or human tracheal epithelial cells; and (c) absence of specific binding to P. aeruginosa pili adhesin.

Particularly useful immunogenic carriers include keyhole limpet hemocyanin (KLH), tetanus toxoid, poly-L-(LYS:GLU), peanut agglutinin, poly-D-Lysine, diphtheria toxoid, ovalbumin, soybean agglutinin, bovine serum albumin (BSA), human serum albumin, and the like.

The peptide may be conjugated to the carrier by a variety of known methods, including chemical derivatization or by standard genetic engineering techniques (e.g., Ausubel).

Vaccines and inocula of the present invention may be administered by injection, usually intramuscularly or subcutaneously, orally by means of an enteric capsule or tablet, as a suppository, as a nasal spray, and by other suitable routes of administration. For a human patient, a suitable dose of the polypeptide depends, in part, upon the chosen route of administration and a number of other factors. Included among those factors are the body weight of the subject to be immunized, the carrier used, the adjuvant used, and the number of inoculations desired to be used.

Individual inoculations for a human patient typically contain unit doses of about 10 micrograms to about 100 milligrams of polypeptide, exclusive of any carrier to which the polypeptide may be linked. If desired, a series of doses may be administered over a period of time for optimum immunity. Unit dosage forms of the vaccine can also be provided, if desired, containing the aforementioned amounts of the polypeptide.

VII. Chimeric Antibodies

The present invention also contemplates a chimeric antibody having variable (antigen-reactive) regions which are immunospecific for the C-terminal region of P. aeruginosa pilin protein, preferably derived from the variable regions of the above mouse monoclonal antibodies PK99H or PK34C, and constant antibody regions from human immunoglobulin constant regions. The chimeric antibody described here is an IgG antibody, it being recognized that other immunogluobulin types, such as IgM antibodies are also suitable.

Figure 18A:
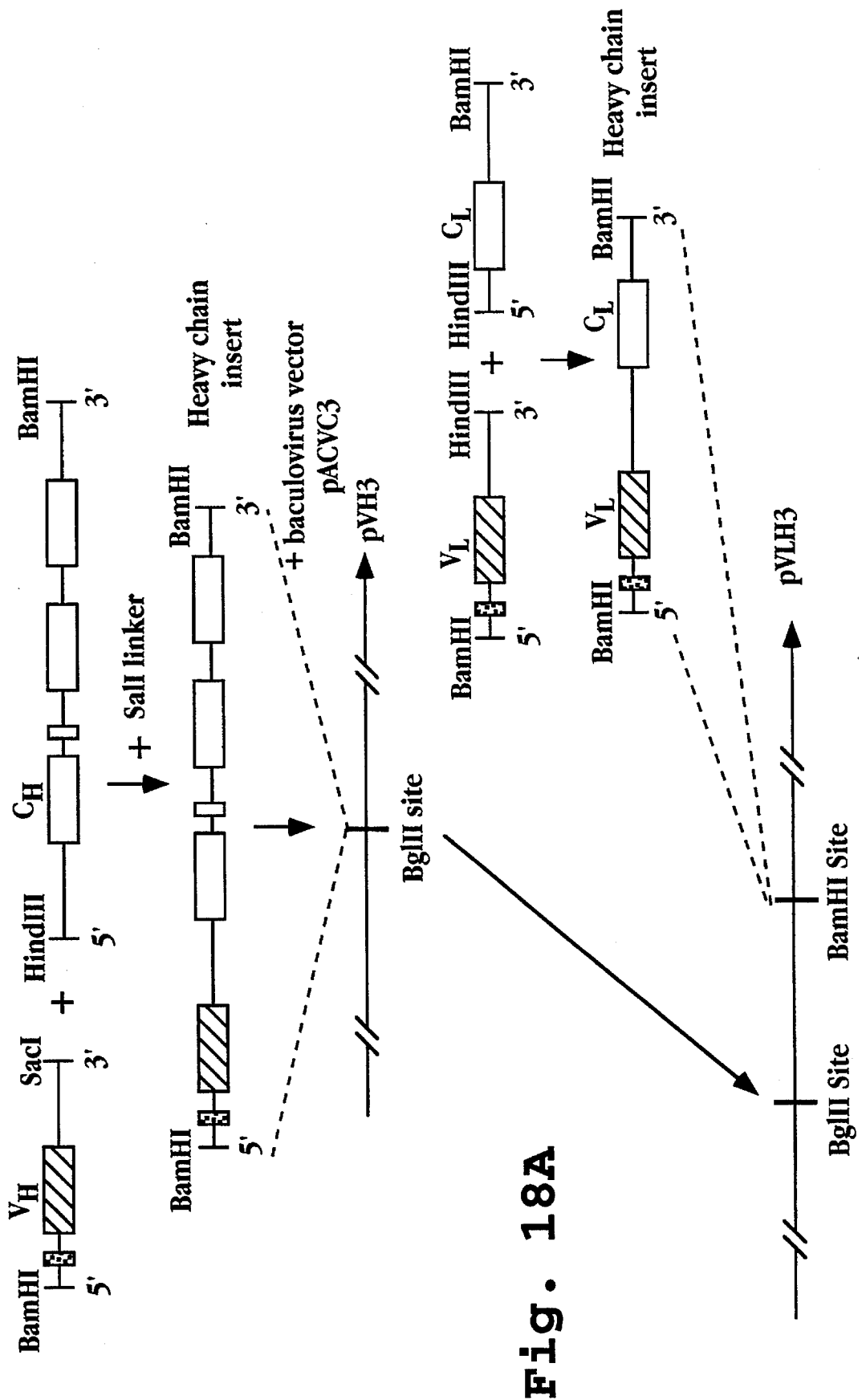
FIG. 18 illustrates recombinant methods suitable for producing a chimeric monoclonal antibody in accordance with the present invention.
Figure 18B:
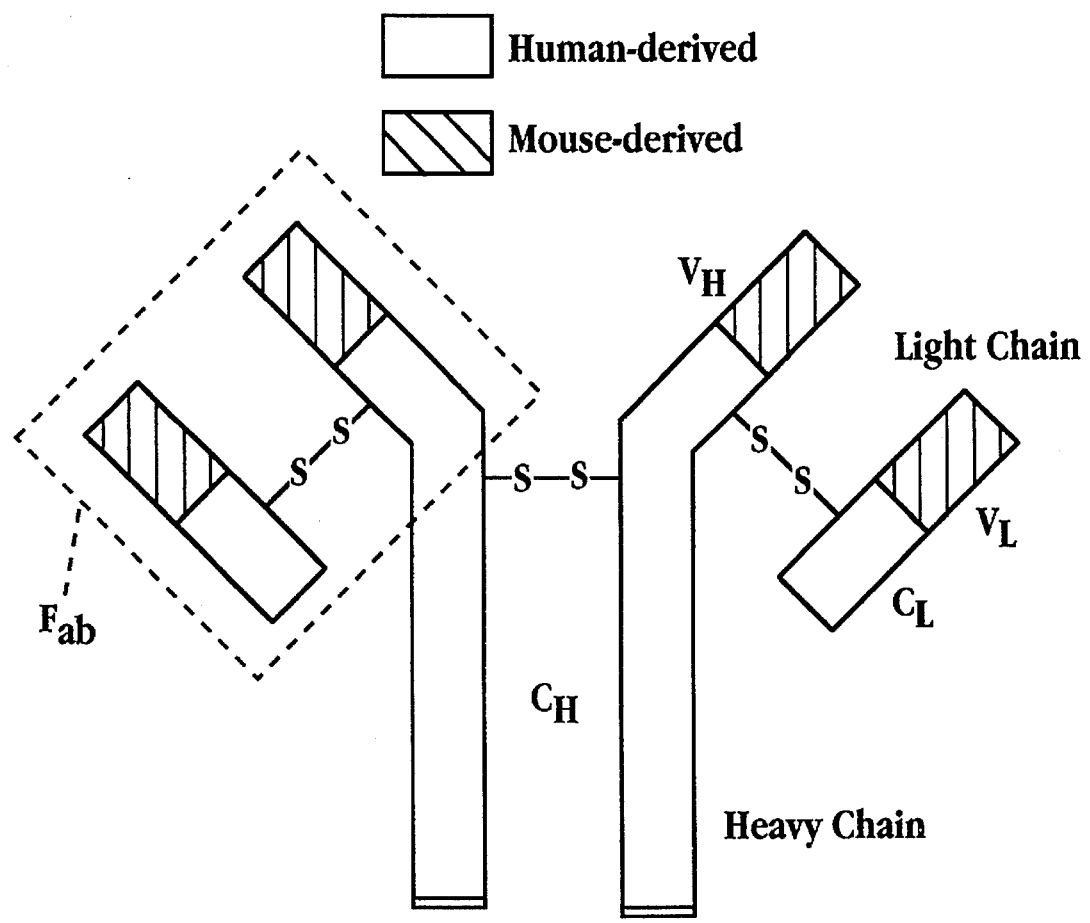

Antibody molecules of the IgG class consist of two heavy (H) chains and two light (L) chains, linked together by disulfide bonds as indicated. As shown in FIG. 18, the variable regions of the antibody molecule consist of portions of both the heavy and light chain polypeptides ($V_H$ and $V_L$). Likewise the constant regions of the molecule consist of portions of both the heavy and light chain polypeptides ($C_H$ and $C_L$). Therefore, in order to construct a chimeric molecule comprising variable regions derived from mouse monoclonal antibodies and constant regions derived from human IgG, partial genes coding for the appropriate portions of the polypeptides must be joined prior to expression of the polypeptide.

Methods for construction of chimeric mouse-human antibodies by recombinant methods are known in the art (Boulianne; Morrison). Suitable expression systems include, but are not limited to prokaryotic and eukaryotic expression systems known in the art. Preferably, the expression system is an insect cell (*Spodoptera frugiperda*) system, which is infected by a recombinant baculoviral vector. Likewise, it will be understood that the recombinant DNA sequences coding for the polypeptide chains of the chimeric antibody can be inserted into separate vectors which are then cotransfected into cells, or they can be inserted into the same expression vector. Preferably, the recombinant DNA sequences are sequentially inserted into a coexpression baculovirus-derived vector (pACVC3) which contains two polyhedrin promoters in opposite orientation which drive the transcription of the inserted gene sequences (zu Pulitz).

FIG. 18 illustrates a preferred construction suitable for use in the baculoviral expression system illustrated. As indicated in the figure, mRNA isolated from a suitable hybridoma cell line, such as cell line PK34C or PK99C, is incubated with a 3' primer to a constant region flanking the variable region of interest and incubated with reverse transcriptase. Gene amplification by polymerase chain reaction (PCR) is carried out using a 5' primer selected from a constant flanking region. This procedure, including appropriate primers for the variable region of the mouse heavy chain ($V_H$), is described by Sastry et al.

The gene coding for VH is preferably subjected to digestion by restriction endonucleases BamHI and SacI to produce a BamHI/SacI (5'–3') fragment. A similar procedure is carried out to obtain the gene fragment coding for the mouse VL region, which is preferably digested with restriction endonucleases BamHI and HindIII to produce a BamHI-HindIII (5'–3') fragment.

Likewise, fragments of genes coding for human heavy and light chain constant regions (CH and CL, respectively) are obtained by methods known in the art (Rabbitts). The $C_H$ containing gene is preferably subjected to digestion by restriction endonucleases HindIII and BamHI to produce a Hind III-Bam HI (5'–3') fragment. The $C_L$ containing gene is preferably subjected to digestion by HindIII and BamHI to produce a HindIII-BamHI ((5'–3') fragment.

A gene coding for a chimeric heavy chain is then obtained by joining the BamHI-SacIDNA fragment coding for $V_H$ with the HindIII/BamHI fragment containing human IgG1 or IgG2 heavy chain constant region ($C_H$) using a SalI linker. A chimeric kappa light chain gene is constructed by joining the BamHI/HindIII fragment containing mouse PK99H or PK34C VL to the HindIII site of a HindIII/BamH1 fragment containing human $C_L$ (Boulianne et al. (Nature 312: 643–646; 1984); Morrison et al (PNAS 81: 6851–6855; 1984)).

The resulting recombinant DNAs are then preferably inserted sequentially into the coexpression baculovirus vector pACVC3 sequentially. First the BamHI fragment coding for the chimeric heavy chain ($V_H$–$C_H$) is inserted into the BglII site of the vector to yield pVH3. The BamHI chimeric light chain gene fragment ($V_L$–$C_L$) is then inserted at a BamHI site of pVH3 to yield pVLH3.

*Spodoptera frugiperda* cells are infected with recombinant baculovirus pVLH3 (Putlitz et al.). Binding capacity of secreted antibodies is analyzed by ELISA as has been described.

The chimeric antibodies produced in accordance with the invention are useful in the treatment or prevention of mammalian infections of Pseudomonas and crossreactive infectious agents, by parenteral administration of the antibodies.

VIII. Peptide Treatment

In one preferred mode of administration, peptides of the invention are delivered by nasal insufflation of powders or atomized solutions containing the peptide. This mode of administration has the advantage that delivery of the peptide is made directly to the pulmonary mucosal epithelial surface.

Yet another use of the peptides of the invention is as target molecules for drug delivery to pulmonary epithelial cells. Since the peptides bind specifically to pulmonary epithelial cells, they are construed to be useful as therapeutic adjuvants in pathological conditions involving the lungs. One such condition is carcinoma of the lung. In one preferred use, the peptides of the invention are conjugated to a photoactivatable chemotherapeutic agent useful in the treatment of lung carcinoma. The drug-peptide conjugate is then administered by nasal insufflation, and the drug is activated by high intensity light delivered through a bronchoscope.

The following examples illustrate methods for preparing and using the peptide and antibody of the invention. The examples are intended to illustrate, but not limit, the scope of the invention.

EXAMPLE 1

Solid-Phase Synthesis of Pilin PAK Peptide

Abbreviations used in this example are BOC, tertiary butoxycarbonyl; DCM, dichloromethane; TFA, trifluoroacetic acid; and BOC-AA-OH, amino acids protected at the alpha amino group by BOC group.

Commercially available phenylacetamidomethyl resin for polypeptide synthesis was obtained from Applied Biosystems (Foster City, Calif.). BOC-AA-OH were obtained from Institute Armand Frappier (Laval, Quebec, Canada). Side-chain protecting groups on the residues are as follows: o-(p-bromobenzoyloxycarbonyl) for tyrosine, o-benzyl for threonine, serine, aspartic acid and glutamic acid; S-methoxy-benzyl for cysteine, 2-chlorobenzyloxycarbonyl for lysine and formyl tryptophane.

A. Solid-phase Synthesis

In preparing a synthetic polypeptide of this invention by the above solid-phase method, the amino acid residues are linked to a resin (solid-phase) through an ester linkage from the carboxy-terminal residue.

Reactive amino acid side chains are also protected during synthesis of the polypeptide. Couplings are typically carried out using a 2-fold molar excess of protected amino acid and one equivalent of dicyclohexyl carbodiimide over the number of milliequivalents of initial N-terminal amino acid. For asparagine (N) and glutamine (Q), 2 molar equivalents of N-hydroxy-benzotriazole and dicyclohexyl carbodiimide were used. Coupling reactions are monitored by the ninhydrin test of Sarin (1981) and are typically more than 99% complete.

B. Oxidation and Purification of the Peptide

The peptide is cleaved from the resin and subsequently cyclized to form a disulfide bond. The cleavage of the peptide and the complete removal of the side-chain protecting groups is accomplished using using anhydrous hydrogen fluoride. The resin is suspended in a mixture containing hydrogen fluoride and anisole (9:1, v/v) and the reaction is allowed to proceed in vacuo for 45 minutes at 5° C. The hydrogen fluoride is then evaporated. The resin is removed and washed with ether (3×10 ml) and the peptide is extracted with 30% acetic acid (3×10 ml). The combined filtrates are diluted to give a 5% aqueous acetic acid solution and lyophilized.

The crude peptide can be purified on an analytical reversed-phase HPLC column (250×4.6 mm internal diameter) using a shallow gradient. The crude peptide was dissolved in the smallest volume of starting buffer possible (about 5 ml). The highly concentrated peptide was centrifuged to sediment undissolved material. An analytical sample, 5–10 µl, was chromatographed using a linear gradient (solvent A is 0.05% aqueous TFA and solvent B is 0.05% TFA in acetonitrile) to determine the total amount of peptide present. When the crude peptide contained hydrophilic and hydrophobic impurities with retention times close to that of the peptide of interest in the analytical run (1% B/min gradient rate), a shallow gradient of 0.2% B/min with a flow rate of 1 ml/min was employed.

The whole stock solution of 30–50 mg was injected onto the column and the run was monitored at 210 nm. Fractions (1 ml) were collected and analysed. Every third or fifth fraction was analysed to identify the region on the chromatogram with the peak of interest. Further analysis of the fractions within this region would then be carried out. The chromatogram of each run could be compared with the initial analytical run prior to purification to ascertain the peak of interest. In this way, the shoulders of the neighboring peaks were eliminated, while fractions of interest were pooled and freeze dried. Dried peptides were stored in glass vial in a dessicator.

Mass spectrometry and HPLC anlysis were used to confirm the PAK peptide structure.

EXAMPLE 2

Preparation of Epithelial Cells

A. Buccal Epithelial Cell (BEC) Preparation

BECs were collected from ten healthy non-smoking male volunteers via wooden application sticks rubbed gently on the inside of cheeks, three wooden application sticks per cheek. These sticks were rubbed gently together in 30 mL phosphate buffered saline to suspend the BECs. These cells were washed three times with 30 mL phosphate buffered saline by successive centrifugation (650×g) and resuspended. The final pellet was suspended in 5 mL phosphate buffered saline at pH 7.2. This suspension was filtered (prewetted 70 μm nylon mesh) and the cells were diluted to a final concentration of $2 \times 10^5$ cells/mL in phosphate buffered saline at pH 7.2. This suspension was stored at 4° C. until ready for use.

B. Tracheal Epithelial Cell Preparation

Human ciliated tracheal epithelial cells (TECs) were obtained from patients in the Surgical Intensive Care unit at Toronto General Hospital by bronchoscopic brushing of the bronchial mucosa as described by Franklin et al. (1987). TECs were obtained by bronchoscopy from surgical patients (under general anesthetic), intubated intensive care unit (ICU) patients, and health volunteers. For the surgical and ICU patients, bronchoscopy was performed with a flexible Olympus Type 2 BF bronchoscope inserted through an endotracheal tube. A cytology brush was used to abrade the tracheal-bronchial mucosa, and TECs were collected in high-glucose Dulbecco modified Eagle medium containing 1% (w.v) sodium citrate.

The cell suspension obtained by bronchoscopy contained both ciliated and nonciliated cuboidal and columnar epithelial cells in addition to various amounts of mucus, erythrocytes, granulocytes, and cell debris and was not suitable for direct use in an adhesion assay. The cell suspension was vortexed briefly, sequentially passed through 70- and 30-micron pore size mesh nylon screens, washed twice (500×g for 15 min at 4° C.) with 10 ml of 0.01M phosphate-buffered saline (pH 7.2) (PBS), and then resuspended in 1 ml of PBS. The cell suspension was then fractionated by density gradient centrifugation (500×g for 15 min at 4° C. in a swinging bucket rotor) on a PBS-preformed (48,000×g for 40 min at 4° C.) 65% (vol/vol) percoll gradient.

The TEC band was collected and applied to a second percoll gradient. The ciliated TEC band was collected from the second gradient, and the cells were washed once in PBS and then resuspended in 1.5 ml of PBS. A direct cell count was performed with a hemacytometer; cell viability was determined by trypan blue dye exclusion. The cell fractionation procedure typically yielded $(2.08\pm0.34) \times 10^5$ cells (mean t standard error), of which 32.8±6.5% were ciliated TECs. The vast majority of these cells were viable, and in many cases the cilia were still beating. The fractionated TECs contained only epithelial cells, were essentially free of contaminating mucus, and were used directly for adhesion assays.

EXAMPLE 3

Polyclonal Antibody Inhibition of Pilus Binding to BECs

A. Preparation of Fab Fragments

Polyclonal antibodies were prepared against the following peptide regions of PAK pilin protein: "r1," :r2," "o1" and "o2," against the reduced (r) or oxidized (o) PAK peptide composed of residues 128–144 of native PAK pilin protein; "22," against residues 22–33; "41," against residues 41–49; "58," against residues 58–70; "75," against residues 75–84; "89," against residues 89–99; "107," against residues 107–116; and "117," against residues 117–125. "Pre" refers to preimmune sera; and "99H" to monoclonal antibody PK99H.

Fab fragments of the above polyclonal sera derived from each peptide antigen were prepared using immobilized papain (Pierce Chemical Co., Rockford, Ill.). Briefly, affinity purified polyclonal antibody was dialyzed against 20 mM cysteine HCl, 10 mM tetrasodium ethylenediaminetetraacetic acid (EDTA) in 20 mM sodium phosphate buffer pH 6.2. Antibody (1 ml containing approximately .2 mg antibody) was added to 0.5 ml immobilized papain and incubated at 37° C. for 20 h with shaking at 150 rpm. The immobilized papain was removed by centrifugation and the supernatant containing the Fab fragments was diluted with 1 ml of PBS.

The Fab fragments were purified by HPLC using a Protein G column eluted with PBS. Fab fragments were collected in the flowthrough, and Fc fragments were eluted from the column with 10 mM glycine pH 2.75. Fab fragments were concentrated by placing the Fab effluent in dialysis tubing (molecular weight cutoff of <8000) and extracting liquid from the dialysis sack using polyethylene glycol (molecular weight of 15,000–20,000). The fragments were then dialyzed against PBS. Activity of Fab fragments was checked by ELISA and production of Fab fragments was confirmed by SDS-PAGE.

B. Inhibition of PAK pilin Binding to BECs by Fab Fragments

PAK pilin protein was isolated according to published methods (Paranchych et al, 1979). Fab fragments, prepared as above, were preincubated with PAK pili before the addition of BECs (1×105 cells/mL final concentration) and pili binding was detected using monoclonal antibody PK38B (which is specific against pilin protein, but not the PAK peptide). All Fabs were diluted such that their final titer as measured by ELISA to PAK pili was $10^{-3}$.

EXAMPLE 4

Monoclonal Antibody Inhibition of *P. aeruginosa* and Pili Binding to BECs

A. Monoclonal Antibodies

Hybridoma cell lines PK99H and PK34C (Doig) were deposited in the cell depository of the Department of Medical and Infectious Diseases of the University of Alberta, Alberta, Canada, and are identified by cell line Nos. PK99H and PK34C. Fab fragment of the PK99H and PK34C Mabs, and non-immune IgG were prepared as described in Example 3A.

B. Inhibition of Pili Binding to BECs

BECs were prepared as described in Example 2. PAK pili were isolated according to published procedures (Paranchych et al., 1979). PAK pilin protein was isolated according to published methods (Paranchych). Fab fragments of PK99H, PK34C, and non-immune IgG were preincubated with PAK pili at the concentrations indicated in Table 1 above (Doig). After incubation, BECs were added to a final concentration of $1 \times 10^5$ cells/mL. Pili binding was detected using monoclonal antibody PK3B, followed by reaction with enzyme-labeled goat anti-mouse antibody, as above. Pili binding, as measured by enzyme activity associated with BECs, is expressed as percent control (no Fab fragments added) in Table 1.

C. Inhibition of *P. aeruginosa* binding to BECs

*P. aeruginosa* strains PAK, PAO, HD1, 492c, P1, K122–4, and PAK/3 are as reported (Doig). Fab fragments of PK99H, PK34C, and normal mouse non-immune IgG were prepared as above. The Fab fragments (0.5 ml of 0 to 3.2 mg/ml) were added to 0.1 ml of bacteria containing $0.7 \times 10^8$ CFU/ml in PBS, and the mixture was incubated for 30 minutes at room temperature. To this mixture was then added 0.4 ml PBS and either 1 ml of BECs containing $2 \times 10^5$ cells or 1 ml PBS (to assess non-specific binding of bacteria to filters. After incubation at 37° C. for 2 hours with shaking, the cells were washed, filtered, and the filters were assayed for the presence of bound bacteria by an ELISA method employing an anti-pilin monoclonal antibody and an enzyme-linked antibody, as described above. The results are shown in Table 2 above.

EXAMPLE 5

Monoclonal Antibody Immunolocalization on Moraxella Cells

Immunolocalization studies employing the polyclonal anti-PAO pili antisera utilized *M. catarrhalis* cells which were absorbed onto the surface of carbon coated, glow discharged electron microscope grids, blocked with 1% (w/v) BSA in PBS pH 7.4 for 2×5 min, and reacted with rabbit anti-PAO pili in PBS pH 7.4 containing 0.5% (w/v) BSA for 35 min at 37° C. The grids were then washed on 5 drops of PBS pH 7.4 containing 0.5% (w/v) BSA, blocked with 1% (w/v) BSA for 2×5 min, reacted with goat anti-mouse IgG-20 nm colloidal gold conjugate (E.Y. Labs Inc., San Mateo, Calif.) in PBS pH 7.4 containing 0.5% (w/v) BSA for 30 min, washed on 5 drops of PBS pH 7.4 containing 0.5% (w/v) BSA, then washed on 5 drops of $H_2O$ and finally blotted dry. The grids were then stained with 1%(w/v) phosphotungstic acid before examination in a Philips EM 401 transmission electron microscope operating at an accelerating potential of 80 kV. Controls included no first antibody and normal mouse IgG (Jackson Laboratories). The polyclonal anti-PAO pili antisera was observed to bind with high affinity to the cell surface and surface appendages of the *Moraxella catarrhalis*.

Immunolocalization studies with monoclonal antibody PK99H were carried out with thin sections of *M. catarrhalis* cells that had previously been embedded in LX12, sectioned, thin sections collected on the surface of 3 mm copper EM grids, and the sections etched with saturated sodium metaperiodate to remove osmium and regain antigenic activity. The thin sections were then treated as described above except that monoclonal antibody PK99H was used instead of the polyclonal antibody. Immunospecific binding of monoclonal antibody PK99H was observed, with the antibody binding both to cell surface components and to cytoplasmic components in the *M. catarrhalis* cell.

EXAMPLE 6

Inhibition of Candida Binding to BECs

A. *C. albicans* culture conditions

The *C. albicans* strains used were isolated from the trachea of intubated intensive care unit patients at Toronto General Hospital, Toronto, Ontario (for fimbrial purification and characterization) or obtained from the Department of Microbiology, University of Alberta Hospital, Edmonton, Alberta.

A loopful of culture from Sabouraud-dextrose agar (Gibco) was used as a source of inoculum for 10 ml of M9 medium (Adams, 1959) supplemented with 0.4% (wt/v) glucose. Two incubation protocols were used. Cultures shaken at 150 rpm were either incubated at 25° C. for 19 hours or for 16 hours at 25° C. followed by a 3-hour incubation at 37° C. Cultures to be used in the radioadhesion assay were supplemented with 55 Ci/ml of [$^{35}$S]-L-methionine (New England Nuclear, Boston Mass.) after 17 hours of incubation. Cells were harvested by centrifugation (12,000×g for 10 min) and washed 3 times with PBS pH 7.2 to remove unincorporated methionine. Washed cells were resuspended in PBS pH 7.2 at varying concentrations. Cells which had been incubated at 37° C. were forcibly passed twice through an 18 gauge needle to break up clumps. No clumping was observed during the adhesion assays.

B. Buccal epithelial cells

BECs were collected with wooden applicator sticks from healthy, non-smoking, male volunteers (n=10). BECs were removed from the applicator sticks by gentle agitation in PBS pH 7.2. The BECs were washed 3 times (2 000×g for 10 min at 4° C.) with PBS pH 7.2, then passed through a 70 μm nylon mesh. The cell concentration for the BECs was determined with a hemocytometer and the BEC concentration was adjusted. The viability of BECs obtained by this procedure was generally about 5%, as determined by trypan blue dye exclusion.

C. *C. albicans* Adherence to Human Ciliated Tracheal Epithelial Cells

Human ciliated tracheal epithelial cells (TECs) were obtained as described by Franklin et al. (1987) and by Todd et al. (1989). Briefly, cells were obtained by bronchoscopy following administration of 5 ml of 1% (w/v) xylocaine to the nasal and oral pharyngeal passages with a further 5 ml of 1% (w/v) xylocaine being administered via the suction port of the bronchoscope at the level of the glottis. An additional 5 ml was further administered within the trachea before repeated (n=10) brushing of the trachea with a disposable cytology brush. Cells were eluted from the brush by agitation in 30 ml of serum free Dubecco's Modified Eagle's Media (high glucose formulation) containing 1% (w/v) sodium citrate and stored at 40° C. before use.

TECs were fractionated from mucus, blood cells, microbial contaminants, and debris by gentle filtration through a 70 μm and a 30 μm nylon mesh, washing the cells three times with 10 ml of PBS pH 7.2 (500×g, at 40° C. for 10 min) concentrating the cells following centrifugation (500× g, at 40° C. for 10 min) in 1 ml of PBS pH 7.2, two sequential density gradient centrifugations on preformed 65% (v/v) Percoll gradients in PBS pH 7.2 (preformed by centrifugation at 48,000×g for 40 min at 40° C.) for 20 minutes at 500×g for 20 min at 40° C., washed twice with 5 ml of PBS pH 7.2, and resuspended in 1 ml of PBS pH 7.2. TECs were quantitated by direct counting employing a hemacytometer.

D. Immunofluorescence of Candida Fimbriae

Yeast were grown at 25° C. or shifted to 37° C. as described above. Yeast were harvested by centrifugation. Cells were fixed with 1.0% formaldehyde in PBS for 30 min and washed twice with PBS. Primary antibody was added and the mixture was incubated at 37° C. for 1 hour, shaking at 300 rpm. Yeast were then collected by centrifugation (12 000×g for 1 min at room temperature) and washed 3 times with PBS pH 7.2. Rabbit anti-mouse IgG (H+L) affinity purified IgG conjugated to fluorescein isothiocyanate (Jackson Laboratories) in PBS pH 7.2 (1/500 dilution) was added to the washed yeast preparations and incubated for 30 min at 37° C., agitating at 300 rpm. The yeast were washed 3 times as described above and resuspended in 0.1 mL of PBS pH 7.2. Wet mounts were prepared, and examined by epifluorescence and phase contrast microscopy using a Lietz Laborlux equipped with a MPS4 camera system. Photographs were recorded with Kodak T-Max film.

E. Adhesion assay

The adhesion assay of McEachran as modified as described by Staddon was used to determine the number of bacteria bound per epithelial cell. BECs (1 mL of $2 \times 10^5$ cells per mL) were mixed with an equal volume of radio-labelled yeast suspended in PBS pH 7.2 and incubated at 37° C. for 2 h, shaking at 300 rpm. Epithelial cells with bound yeast were then collected by filtration on 5 micron polycarbonate filters (Nuclepore) pretreated with 2% (w/v) bovine serum albumin (BSA) in PBS pH 7.2 to reduce nonspecific binding, washed with 15 mL PBS pH 7.2 and then placed in scintillation vials. Aquasol (5 mL) was added to each vial and the amount of radioactivity was determined by scintillation counting in a Beckman LS-150 liquid scintillation counter. Triplicate aliquots were filtered for each sample. Binding of yeast to epithelial cells was corrected for nonspecific binding of yeast to the 12 μm filter (nonspecific binding was generally less than 15% of the experimental value). The epithelial cell concentration was determined at the end of the assay to correct for cells lost during incubation.

Total and viable cell counts were performed before and after the adhesion assay. Total cell counts were determined using a hemacytometer. Viable counts were determined by serially diluting C. albicans in PBS pH 7.2 and plating appropriate dilutions on Sabouraud-dextrose agar (Gibco) which were incubated at 37° C. until visible and countable colonies formed (usually 24 to 48 hours).

F. Purification of Candida Fimbria

C. albicans were cultured in M9 medium (Adams, 1959) supplemented with 0.4% (wt/v) glucose overnight at 37° C. at 150 rpm. This culture was used to inoculate Sabouraud-dextrose agar (Gibco) in aluminum trays (approximately 2 ml/tray). The trays were incubated at 37° C. for 5 days. Yeast cells were then scraped from the surface of the agar with a bent glass rod and suspended in PBS pH 7.2 containing 1 mM phenylmethylsulfonyl fluoride (Sigma) as a protease inhibitor. Fimbriae were then sheared from the cell surface by blending (4×15 second cycles using a Waring blender). Cells were examined by phase microscopy and appeared to be intact.

Cells were removed by centrifugation (12,000×g for 20 min.) and by subsequent filtration of the supernatant through a 0.45 μm polycarbonate filter (Nuclepore Corp., Pleasanton, Calif.). The supernatant was placed in dialysis tubing (Spectrum, Los Angeles, Calif.; M.W. cut off 6000–8000 Da) and concentrated with polyethylene glycol (M.W. 15,000–20,000, Sigma) (PEG). Finally the sample was dialyzed against PBS pH 7.4. The final preparation was termed crude fimbriae (CF) and was stored at −70° C.

Crude fimbriae were purified by HPLC size exclusion chromatography on a Protein-Pak 300 SW column (Millipore Inc.) having a size exclusion limit of 300,000 daltons operating at 0.5 ml/min flow rate and previously equilibrated with PBS pH 7.2 buffer containing 1 mM $CaCl_2$ and eluted with the same buffer. Purified fimbriae were obtained by re-chromatographing the material that initially eluted in the void volume of the column and collecting the material that still eluted within the void volume from the second chromatographic run. Purified fimbriae consisted of ~15% (w/w) protein and ~85% carbohydrate (w/w) on the basis of colorimetric assays and consisted of a single polypeptide of ~64,000 daltons on the basis of SDS-polyacrylamide gel electrophoretic analysis utilizing silver staining (see figures).

G. Effect of Candida fimbriae on PAK pilus binding to BECs

An immunoassay was performed to assess the effect of Candida fimbriae binding of pili from PAK to BECs. BECs (1 mL at $2.0 \times 10^5$ BECs/mL), PAK pili (0.5 mL of 80 ug/mL), and fimbriae (0.5 mL of 400 or 800 ug/mL) in PBS pH 7.2 were mixed and incubated at 37° C., shaking at 300 rpm in a New Brunswick gyroshaker. After 1 h BECs were collected by centrifugation (12 000×g for 10 min at 4° C.) and washed twice with PBS pH 7.2. Anti-PAK pilus monoclonal antibody PK3B (Doig et al. 1990) was added to the BEC pellet (1 mL of a $10^{-4}$ dilution) and incubated as described above for 1 h. The BECs were then collected by centrifugation and washed twice with PBS pH 7.2. Goat anti-mouse IgG(H+L) peroxidase conjugate (Jackson Laboratories) was added to the BEC pellet (1 mL diluted per instructions for use) and the mixture was incubated as described above for 1 h. The BECs were collected by centrifugation, transferred to a clean test tube, and washed twice with PBS pH 7.2. The pellet was resuspended in 1 mL of a solution containing 1 mM 2,2'-azinobis[3-ethylbenzothiazoline-6-sulfonic acid], 0.03% (vol/vol) in 10 mM citrate buffer pH 4.2. The reaction was stopped by the addition of 1 mL of 4 mM $NaN_3$ and the optical density at 405 nm was determined after removal of the BECs by centrifugation. The BEC concentration in each tube was determined with a hemocytometer at the end of the assay prior to the removal of BECs by centrifugation.

H. Assessment of PAK pilus or Candida fimbriae inhibition of Candida binding

Pili and fimbriae inhibition assays were performed using a direct competition method. Direct competition of pili/fimbriae and yeast was achieved by the simultaneous addition of pili/fimbriae, yeast and BECs at the commencement of the yeast binding assay. The number of yeast bound per BEC was determined as described above.

EXAMPLE 7

Pseudomonas/Candida Antibody Crossreactivities

A. Enzyme-linked immunosorbant assay (ELISA)

Antigens were coated on NUNC 96-well polystyrene wells. Antigen (10 ug/mL in 0.01M carbonate buffer, pH 9.5) was added to each well (100 μl/well) and left for 6 h at room temperature. Wells were then washed 3 times with 250 μl of PBS pH 7.4 supplemented with 0.02% (wt/vol) BSA (buffer A). Wells were blocked with 5% (wt/vol) BSA in PBS pH 7.4 overnight at 4° C. Wells were washed three times and 100 μl of primary antibody was added for 2 h. Each well was then washed 3 times with 250 μl buffer A using aspiration. A goat anti-mouse IgG (H+L) immunoglobulin-horse radish peroxidase conjugate (Jackson Laboratories) in buffer A (100 μl/well) was added and incubated for 2 h at room temperature. The wells were washed 3 times with buffer A and 250 51/well substrate solution (1 mM 2,2'-azino-di-(3-ethylbenzthiazoline sulfonic acid), 0.03% (vol/vol) hydrogen peroxide in 10 mM sodium citrate buffer pH 4.2) added. The reaction was stopped by the addition of 250 μl/well of 4 mM sodium azide and absorbance at 405 nm determined using an EL-407 plate reader.

B. Competitive ELISA

Competitor and antibody were mixed together in 10 mM PBS pH 7.2 buffer containing 0.05% (w/v) BSA and incubated for 30 min at room temperature. The conditions of the assay were such that ~50% of the antigen immobilized on the ELISA plate surface would be bound with antibody if there was no competitor present. The mixture of antibody and competitor was then added to wells (100 μl/well) coated with PAK pili or Candida fimbriae and blocked with BSA as described above. The ELISA was then performed as described above. The apparent affinity of the antibody for the competitor was determined as described by Nieto et al. (1984) following determination of the concentration of competitor that would give 50% inhibition of antibody binding to antigen.

C. Whole Cell *C. albicans* Dot Blots

Dot blots were performed using a Bio-Rad dot blotting manifold. Whole cells of various clinical isolates of Candida albicans were initially washed 3 times with PBS pH 7.2 buffer and 100 μl of cell suspension containing $2 \times 10^6$ CFU was added per well on a pre-wetted nitrocellulose membrane. The cells were collected on the surface of the filter by vacuum filtration. The wells were washed 4 times with 0.1% (vol/vol) Tween 20, 50 mM Tris buffered saline pH 7.5 (TTBS) (200 μl/well) and blocked with 100 μl of 3% (wt/vol) BSA in TTBS for 1 h. The wells were then washed 4 times with TTBS and monoclonal antibody PK99H and PK34C at various dilutions in TTBS were added (100 μl/well) and incubated for 1 h. The blot was washed 4 times with TTBS and 100 51 of a goat anti-mouse IgG (H+L) immunoglobulin-alkaline phosphatase conjugate in TTBS was added to each well for 1 h. After washing the blot 6 times with TTBS, a substrate solution consisting of 0.33 mg/mL nitro blue tetrazolium chloride, 0.165 mg/mL 5-bromo-4-chloro-3-indolyl-phosphate, 100 mM sodium chloride, 5 mM magnesium chloride, 100 mM Tris buffer pH 9.5 was added. Color development was stopped by aspiration and rinsing the membrane in distilled water.

D. Assessment of antibody Fab fragments on yeast binding:

Effect of Fab fragments on binding was performed as follows. Fab fragments (0.5 mL of 800 μg/mL in PBS pH 7.2) were added to 0.1 mL of yeast in PBS pH 7.2 and incubated for 30 min at room temperature. To this 0.4 mL of PBS pH 7.2 and either 1.0 mL of BECs ($2 \times 10^5$ cells/mL) or 1.0 mL of PBS pH 7.2 was added. The mixture was then incubated at 37° C. shaking at 300 rpm for 2 h. The remainder of the adhesion assay was performed as described above.

EXAMPLE 8

Preparation of Random-Sequence Peptide

A. Construction of epitope library for peptide ligands

An epitope library which approximately $10^8$ novel heptapeptide sequences is constructed as described by Scott and Smith. Alternatively a similar epitope library can be constructed as described by Cwirla et al or Devlin et al. FIG. 17 shows a schematic representation of the construction of the library as described by Scott and Smith and summarized here.

Filamentous phage fUSE5 is constructed as a vector for the epitope library as described by Parmley and Smith (1988; Gene 73: 305–318) and by Scott and Smith. This phage contains a tetracycline resistance gene, and is designed to have cloning sites, insertion into which result in addition of peptide sequence at the exposed N-terminus of the minor capsid protein pIII. Addition of foreign peptide sequence at this site does not substantially inhibit infectivity of the phage. However its location does make it exposed on the surface of the phage and thus amenable to recognition by antibodies.

In preparation for ligation with a foreign DNA fragment, fUSE5 is digested with Sfi I (BRL; 120 units/30 ug fUSE5 RF DNA). Following extraction with phenol and chloroform, the volume is adjusted to approximately 0.8 ml with TE buffer (10 mM Tris pH 8, 1 mM EDTA), and the DNA is precipitated by additions of sodium acetate buffer (3M; pH 6) and isopropanol. Following incubation (20 min at 0 degrees) and pelleting, the pellet is washed with 70% (v/v) ethanol, redissolved in TE buffer, ethanol precipitated and redissolved in TE.

An insert containing a random heptapeptide sequence is prepared by polymerase chain reaction (PCR) amplification of a 73 base degenerate template shown in FIG. 17 with 5' biotinylated primers corresponding to the first 20 bases at the 5'ends of both strands shown in FIG. 17 (top). The template is then cleaved at the two BgII sites shown and then adsorbed onto streptavidin-agarose to remove the biotinylated terminal fragments along with the undigested and partially digested by-products. The PCR mixture contains 1 μg of template, 5 μg of each of the biotinylated primers, and 25 units of AmpliTaq DNA polymerase (Perkin-Elmer/Cetus).

The mixture is subjected to five temperature cycles (2.5 min. at 95 degrees, 4 min. at 42 degrees, 4.4 min. at 72 degrees, 5 min. at 72 degrees), then the reaction is stopped by addition of EDTA solution (final concentration, 1 mM), pH 8. Following precipitation with ethanol and dissolution in 0.1 ml TE buffer, a portion of the product is digested with Bgl I (Promega; 6.4 units/ul final concentration) for 2 hours at 37 degrees to produce a 36 bp degenerate fragment. The randomly selected codons in this fragment are represented by $(NNK)_7$, where N stands for an equal mixture of deoxynucleotides G, A, T, and C, and K stands for an equal mixture of G and T. M stands for an equal mixture of C and A in the complementary strand. NNK therefore represents an equal mixture of 32 triplets, including codons for the 20 amino acids plus the amber stop codon. The digestion by Bgl I is stopped by addition of EDTA solution (10 mM, final concentration). Pre-washed streptavidin beads are then added to the solution and mixed for 30 minutes, and removed by centrifugation. This step is repeated with fresh steptavidin beads. The final product is extracted (phenol plus chloroform) and evaporated to a volume of 0.1 ml.

Ligation of the insert to the SfiI digested fUSE5 RF is carried out in a volume of 2 ml. The reaction mixture consists of 36 μl of the degenerate 36 bp insert and 10 ug of the Sfi I digest of fUSE5. The product is extracted with phenol and chloroform, ethanol precipitated, and dissolved in 0.2 ml TE buffer.

The ligation product is electroporated into *E. coli* MC1061 cells for amplification of phage carrying degenerate peptide sequences. Following electroporation, the bacteria are diluted into growth medium containing tetracycline. Tetracycline resistance of cells indicates successful transfection.

B. Selection of Antibody-Binding Peptide

Phage are isolated from plate stocks by scraping from the agar surface, resuspending in L broth and clearing the supernatant twice by centrifugation (8000 rpm for 10 minutes in a Beckman JA10 rotor at 4 degrees). Phage particles are precipitated with polyethylene glycol (3.3%) in 0.4M NaCl, followed by centrifugation. Phage pellets are resuspended in TBS buffer (50 mM Tris-HCl, pH 7.5, 150 mM NaCl) and stored at 4 degrees.

Phage are affinity purified using the monoclonal antibodies PK34C or PK99H in a panning procedure. Alternatively, FAb fragments of these antibodies are used in this procedure. Briefly, after incubation of phage ($10^{11}$–$10^{12}$ infectious particles) overnight with 1 ug of purified antibody, phage expressing peptides with affinity for the antibodies or their Fab fragments are isolated using the panning method of Parmley and Smith. Biotinylated goat anti-mouse antibodies are added to the mixture, and the mixture is then added to a streptavidiin coated plate. This procedure can also be carried out without use of the second (goat) antibodies, by directly biotinylating the primary antibodies of Fab fragments. Following incubation (10–30 minutes) the streptavidin-coated plate is washed, and adherent phage are eluted for 10 minutes in a buffer containing 0.1M HCl (pH 2.2, adjusted with glycine) and bovine serum albumin (1 mg/ml). Neutralization of the eluate is achieved using an aliquot of 2M Tris. Eluted phage are then amplified by infection of E.coli, followed by incubation on agar plates containing tetracycline. The resulting amplified phage pool is repurified twice by the same panning procedure described above.

Phage selected through 2–3 rounds of panning are cloned and propagated, and their DNA's are sequenced using standard techniques to determine the amino acid sequences of their peptide epitopes.

Although preferred embodiments of the invention are described herein in detail, it will be understood by those skilled in the art that variations may be made thereto without departing from the spirit of the invention or the scope of the appended claims.

It is claimed:

1. A composition for use as a vaccine against infection by *P. aeruginosa* comprising
    (A) a peptide consisting essentially of an amino acid sequence selected from the group consisting of SEQ ID NO:11, SEQ ID NO:12, SEQ ID NO:13, SEQ ID NO:14, and SEQ ID NO: 15, and
    (B) a carrier protein to which the peptide is covalently attached.

* * * * *